(12) United States Patent
Xu et al.

(10) Patent No.: US 6,895,340 B2
(45) Date of Patent: May 17, 2005

(54) METHOD OF MOLECULAR STRUCTURE RECOGNITION

(75) Inventors: Feng Xu, Cheshire, CT (US); Steven E. Klohr, Glastonbury, CT (US); David Detlefsen, New Hope, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 192 days.

(21) Appl. No.: 10/120,738

(22) Filed: Apr. 11, 2002

(65) Prior Publication Data

US 2002/0173920 A1 Nov. 21, 2002

Related U.S. Application Data

(60) Provisional application No. 60/286,716, filed on Apr. 25, 2001.

(51) Int. Cl.[7] .............................................. G01N 31/00
(52) U.S. Cl. ............................ 702/27; 702/19; 702/31; 702/79; 424/9.3; 424/9.361; 324/307; 324/310; 436/1; 436/2; 436/50; 436/55; 600/410; 600/416; 505/844; 505/845
(58) Field of Search ........................ 702/19, 27, 31–32, 702/75, 76, 179–180, 189, 190, FOR 103, 104, 107, 115, 121, 139, 155, 157, 170, 171; 424/9.3, 9.361; 324/307, 310, 311, 317, 248; 436/1, 2, 50, 55, 173; 600/410, 416; 505/844, 845

(56) References Cited

U.S. PATENT DOCUMENTS

| | | | |
|---|---|---|---|
| 4,719,582 A | * | 1/1988 | Ishida et al. ................. 364/498 |
| 5,025,388 A | | 6/1991 | Cramer, III et al. |
| 5,121,337 A | | 6/1992 | Brown ....................... 364/498 |
| 5,218,529 A | | 6/1993 | Meyer et al. |
| 5,420,508 A | | 5/1995 | Smith |
| 5,446,681 A | | 8/1995 | Gethner et al. ............. 364/554 |
| 5,610,836 A | | 3/1997 | Alsmeyer et al. ........... 364/498 |
| 6,027,941 A | | 2/2000 | Jarvie et al. ................ 436/173 |
| 6,421,612 B1 | * | 7/2002 | Agrafiotis et al. ............ 702/19 |

FOREIGN PATENT DOCUMENTS

WO    WO 00/47992    8/2000

OTHER PUBLICATIONS

Yehia et al., "A Parameteric Three–dimensional Model of The Vocal–Trackt Based On MRI Data", Jan. 1997, IEEE, pp. 1619–1622.*

Varmuza, "From MS Data via Chemometrics to Chemical Structure Information", Jan. 2001, ESMS Lecture, pp. 1–11.*

Pickett, et al., Diversity Profiling and Design Using 3D Pharmacophores: Pharmacophore–Derived Queries (PDQ), J. Chem. Inf. Comput. Sci., 1996, vol. 36, pp. 1214–1223.

(Continued)

Primary Examiner—Marc S. Hoff
Assistant Examiner—Elias Desta
(74) Attorney, Agent, or Firm—James Epperson

(57) ABSTRACT

An analytical method and apparatus using principal component analysis of nuclear magnetic resonance (NMR) data for rapid molecular structure/function pattern recognition. The presence of a molecular substructure in an organic compound is determined by comparing principal components calculated from chemical shift values of the substructure in selected compounds with those calculated from the chemical shift values of the organic compound. Alternatively, principal components are calculated from the intensities of NMR signals for a full spectrum, or selected regions thereof, to determine whether an organic compound belongs to or is excluded from a set of structurally related compounds. Also, the presence of a pharmacophore in an organic compound can be determined by comparing the principal components derived from data on a set of compounds known to bind to a particular receptor, or have a common biological effect, with the principal components of the data set of the organic compound.

18 Claims, 18 Drawing Sheets

OTHER PUBLICATIONS

Silverstein, et al., Spectrometric Identification of Organic Compounds, 6th ed., 1998, John Wiley & Sons, Inc. (table of contents).

Belton, et al., "Application of chemometrics to the 1H NMR spectra of apple juices: discrimination between apple varieties," Food Chemistry, vol. 61, No. 1/2, pp. 207–213, 1998.

Holmes, et al., "Chemometric Models for Toxicity Classification Based on NMR Spectra of Biofluids," Chem. Res. Toxicol., 13, pp. 471–478, 2000.

Holmes, et al., "The identification of novel biomarkers of renal toxicity using automatic data reduction techniues and PCA of proton NMR spectra of urine," Chemometrics and Intelligent Laboratory Systems, 44, pp. 245–255, 1998.

Spraul, et al., "Flow Injection Proton Nuclear Magnetic Resonance Spectroscopy Combined with Pattern Recognition Methods: Implications for Rapid Structural Studies and High Throughput Biochemical Screening," Analytical Communications, 34, pp. 339–341, Nov. 1997.

Malkavaara, et al., "Chemometrics: An Important Tool for the Modern Chemist, and Example from Wood–Processing Chemistry," J. Chem. Inf. Comput. Sci., 40, pp. 438–441, 2000.

Ebert, et al., "Multivariate Investigation of 1H and 13C NMR Shifts of 2– and 3–Substituted Furans, Thiophenes, Selenophenes and Tellurophenes," Magnetic Resonance in Chemistry, 28, pp. 397–407, 1990.

* cited by examiner

| PCA-No. | Compound ID | H1 | H2 | H3 | |
|---|---|---|---|---|---|
| 1 | 26837 | 6.65 | 7.68 | 7.75 | |
| 2 | 26838 | 6.64 | 7.68 | 7.75 | |
| 3 | 26839 | 6.62 | 7.62 | 7.72 | |
| 4 | 26840 | 6.63 | 7.63 | 7.72 | |
| 5 | 26841 | 6.55 | 7.68 | 7.73 | |
| 6 | 26842 | 6.56 | 7.65 | 7.74 | |
| 7 | 26843 | 6.65 | 7.68 | 7.78 | |
| 8 | 26844 | 6.62 | 7.62 | 7.74 | |
| 9 | 26845 | 6.64 | 7.67 | 7.76 | |
| 10 | 26846 | 6.63 | 7.68 | 7.76 | |
| 11 | 26847 | 6.66 | 7.68 | 7.77 | |
| 12 | 26848 | 6.64 | 7.69 | 7.76 | test compound |

FIG. 5

| | | | | | |
|---|---|---|---|---|---|
| 1 | 9235 | 6.52 | 7.36 | 7.83 | |
| 2 | 9236 | 6.67 | 7.31 | 7.86 | |
| 3 | 9237 | 6.66 | 7.26 | 7.84 | |
| 4 | 9238 | 6.63 | 7.24 | 7.38 | |
| 5 | 10516 | 6.9 | 7.53 | 8.21 | |
| 6 | 10536 | 6.97 | 7.57 | 8.28 | |
| 7 | 14507 | 6.72 | 7.36 | 7.93 | |
| 8 | 19459 | 6.93 | 7.64 | 8.18 | |
| 9 | 26848 | 6.64 | 7.69 | 7.76 | test compound |
| 10 | 36853 | 6.7 | 7.25 | 7.92 | |
| 11 | 79785 | 6.34 | 7.24 | 7.31 | |
| 12 | 79788 | 6.33 | 7.24 | 7.32 | |

FIG. 6

| No. | Name | H8 | H12 | H14 | H15 |
|---|---|---|---|---|---|
| 1 | HSYRCDL_6 | 5.2 | 3.64 | 1.28 | 1.28 |
| 2 | HSYRCDL_8 | 4.99 | 3.54 | 1.5 | 1.16 |
| 3 | HSYRCDL_10 | 5.01 | 3.88 | 1.66 | 1.33 |
| 4 | HSYRCDL_68 | 5.09 | 3.59 | 1.55 | 1.21 |
| 5 | HSYRCDL_70 | 4.86 | 3.53 | 1.63 | 1.27 |
| 6 | HSYRCDL_116 | 4.74 | 3.96 | 1.49 | 1.49 |
| 7 | ID_36127 | 4.75 | 3.58 | 1.64 | 1.35 |
| 8 | ID_3941 | 4.25 | 2.92 | 1.67 | 1.32 |
| 9 | ID_3942 | 4.38 | 3.02 | 1.67 | 0.99 |
| 10 | ID_81434 | 4.34 | 2.98 | 1.36 | 1.36 |
| 11 | ID_81435 | 4.79 | 3.93 | 1.3 | 1.3 |
| 12 | ID_4079 | 4.49 | 3.51 | 1.61 | 2.48 |
| 13 | ID_4090 | 5.02 | 3.5 | 1.61 | 1.36 |
| 14 | ID_4091 | 5.14 | 3.5 | 1.61 | 1.35 |
| 15 | ID_4092 | 5.02 | 3.38 | 1.45 | 1.37 |
| 16 | ID_4093 | 5.21 | 3.53 | 1.61 | 1.37 |
| 17 | ID_119 | 4.53 | 3.03 | 1.68 | 1.68 |
| 18 | ID_131 | 4.72 | 3.1 | 1.3 | 2.1 |

\* Compounds 1-6 are the training set and Compounds 7-18 are the test compounds.

METHOD OF MOLECULAR STRUCTURE RECOGNITION

CROSS REFERENCE TO RELATED APPLICATION

This non-provisional application claims priority from provisional application U.S. Ser. No. 60/286,716 filed Apr. 25, 2001.

FIELD OF THE INVENTION

The present invention relates to a method for elucidating structural information about an organic molecule utilizing statistical analysis of spectral data. In particular, the present invention relates to an analytical method which uses principal component analysis (PCA) of nuclear magnetic resonance (NMR) data for rapid molecular structure/function pattern recognition.

BACKGROUND OF THE INVENTION

Principal component analysis (PCA) is a well-known multivariate statistical technique for reducing the number of correlated variables to a smaller number of independent variables, known as principal components. PCA transforms the original set of variables into a smaller set of principal components that account for most of the variance of the original data set, thereby reducing the dimensionality of the data. The components are rank ordered in terms of the variability they represent with respect to the original variables. PCA has traditionally been used with a group of closely related data as a training set to generate a principal component defined model of the correlated variables, which is in turn used to predict membership of an unknown entity based on its relationship to the PCA-based model. The independent principal components are used in place of the original dependent variables for plotting, regression, clustering, and the like.

Nuclear magnetic resonance (NMR) is a phenomenon that is based on the magnetic properties of nuclei such as hydrogen-1, carbon-13 and phosphorous-31. When these nuclei are placed in a static magnetic field and are subjected to electromagnetic radiation, the nuclei absorb the radiation's energy at certain frequencies characteristic of each nucleus. Pulsed NMR is a well known technique which uses a burst or pulse of energy to excite the nuclei of a target atom in an essentially static magnetic field. After the application of the pulse of radio frequency (RF) radiation, all of the nuclei excited re-emit RF radiation at their respective resonance frequencies. The emission over time, known as free induction decay (FID), is measured and the frequencies are extracted from the FID by a Fourier transform of the time-based data.

NMR has been widely used for molecular structure determination. Because the resonance frequency of each NMR-active nucleus is typically determined by its surrounding environment in the molecular structure, structural information of a molecule can be determined by correlating NMR spectral features of the NMR-active nuclei in the molecule. See, for example, R. M. Silverstein and F. X. Webster, "Spectrometric Identification of Organic Compounds," John Wiley & Sons, Inc. (sixth edition), 1998.

PCA techniques have been used to analyze NMR data obtained from mixtures of substances in order to compare an unknown mixture to a standardized mixture. Such techniques have been used to assure the standardization of juices, oils, and plant material. As an example, International Patent Application WO 00/47992, assigned to Oxford Natural Products PLC, discloses the use of NMR spectroscopy combined with computer-based pattern recognition statistical procedures to analyze mixtures of medicinal plant material for consistency in content and bioactivity with a reference mixture. The spectrum of a known standard sample of the material (possessing the desired property) is compared with the spectrum of an unknown sample to determine the similarity of the two materials.

U.S. Pat. No. 5,446,681 ('681) assigned to Exxon Research and Engineering Company describes a method of estimating physical property and/or composition data of a mixture via on-line spectral measurement using a computer controlled spectrometer, followed by statistical analysis of the resultant data compared with a statistical model using sample calibration data. This comparison permits automatically classifying a sample based upon statistical and rule-based criteria.

These methods rely on spectral data derived from samples having known compositions which are then compared to those of an unknown composition in order to estimate an identity/property of the unknown composition. See also:

P. S. Belton, I. J. Colquhoun, E. K. Kemsley, I. Delgadillo, P. Roma, M. J. Dennis, M. Sharman, E. Holmes, J. K. Nicholson and M. Spraul, "Application of chemometrics to the 1H NMR spectra of apple juices: discrimination between apple varieties," Food Chemistry, 1998, 61, 207–213 (PCA and linear discriminant analysis to predict membership amongst apple varieties); and E. Holmes, A. W. Nicholls, J. C. Lindon, S. C. Connor, J. C. Connelly, J. N. Haselden, S. J. P. Damment, M. Spraul, P. Neidig and J. K. Nicholson, "Chemometric Models for Toxicity Classification Based on NMR Spectra of Biofluids," Chem. Res. Toxicol, 2000, 13, 471–478 (1H-NMR spectroscopic and pattern recognition-based methods-including PCA—were used to compare rat urine samples).

E. Holmes, J. K. Nicholson, A. W. Nicholls, J. C. Lindon, S. C. Connor, S. Polley, and J. Connelly, in "The identification of novel biomarkers of renal toxicity using automatic data reduction techniques and PCA of proton NMR spectra of urine," Chemometrics and Intelligent Laboratory Systems, 1998, 44, 245–255, describe a technique which utilizes PCA of $^1$H-NMR spectroscopy to predict drug toxicity. A method analyzes urine samples by comparing NMR data to that of reference urine samples having standardized toxicity spectra. The presence or absence of key regions, or markers, of region-specific toxicity is made by comparison of test urine samples with the standards to assess whether a potential drug may be toxic.

See also M. Spraul, M. Hofmann, M. Ackermann, A. W. Nicholls, S. J. P. Damment, J. M. Haselden, J. P. Shockcor, J. K. Nicholson, and J. C. Lindon, "Flow Injection Proton Nuclear Magnetic Resonance Spectroscopy Combined With Pattern Recognition Methods: Implications for Rapid Structural Studies and High Throughput Biochemical Screening," Analytical Communications, November 1997, 34, 339–341 (High throughput analysis of urine samples to identify drug toxicity).

PCA techniques have been used in analyses of NMR data relating to wood processing. One technique examines aliphatic and phenolic hydroxyl groups in the lignin of wood liquors to confirm the cleavage of Beta-aryl-ethers in native lignin during kraft pulping. NMR data from both carbon-13 and phosphorous-31, along with additional data, are used to predict the overall effects of kraft pulping using multivariate techniques including PCA. This technique, which does not analyze molecular structure, is described by P. Malkavaara, R. Alen, and E. Kolehmainen in "Chemometrics: An Important Tool for the Modern Chemist, an Example from Wood-Processing Chemistry," *J. Chem. Inf. Comput. Sci.* 2000, 40, 438–441.

PCA techniques are also used to calibrate NMR spectrometers in order to assure consistency across trials. U.S. Pat. No. 5,420,508 ('508) assigned to Auburn International, Inc. describes a pulsed NMR analysis system and process comprising an on-line system to extract a sample and establish digitized FID curves, from which curve components functions are determined using regression techniques including PCA to correlate the curve components to the target nuclei, crystalline or amorphous, and to analyze other material characteristics, such as flow rates in plastic. This technique, while assuring proper calibration of the pulsed NMR analysis system, does not examine chemical structure.

U.S. Pat. No. 5,121,337 assigned to Exxon Research and Engineering Company describes both calibration and correction of spectral data and the analysis of an unknown sample using statistical techniques including Principal Component Regression (PCA followed by regression analysis). Data correction deals with baseline variations or ex-sample chemical contamination. The analysis method predicts mixture properties such as: component concentrations, API gravity, estimation of cetane number for petroleum mid-distillates, estimation of hydrogen contents of mid-distillates, calibration of the apparatus with reference to mixture spectra, and component estimation of an unknown composition which is compared to a known standard mixture.

Another calibration technique is disclosed in U.S. Pat. No. 5,610,836, assigned to Eastman Chemical Company, which utilizes PCA in connection with spectrum analysis to compensate for sample volume discrepancies or other interferences that prevent correct quantitative analysis of samples.

NMR methods coupled with statistical analysis have been used to reveal the protein counterpart of a pharmacophore. U.S. Pat. No. 6,027,941 ('941) assigned to CuraGen Corporation discloses a method for obtaining distance measurements of known proteins/chemical compounds using solid-state NMR data subjected to statistical analysis methods to provide information for the elucidation of structures of pharmaceutical lead compounds, drug molecules, or their targets. This technique requires labeling of the known proteins/chemical compounds tested in order to produce a highly accurate three dimensional analysis thereof, but does not provide an automated method to identify whether or not a chemical compound is a potential pharmaceutical lead compound.

Analytical methods have used PCA coupled with other techniques in order to generate information pertaining to the structure of organic compounds. C. Ebert, T. Gianferrara, P. Linda and P. Masotti, in "Multivariate Investigation of $^1$H and $^{13}$C NMR Shifts of 2- and 3-Substituted Furans, Thiophenes, Selenophenes and Tellurophenes," *Magnetic Resonance in Chemistry*, 1990, 28, 397–407, indicate that PCA alone is appropriate only for classification problems and not for prediction of chemical shifts (or identification of chemical structure). In that reference, PCA coupled with a partial least squares (PLS) analysis was used to predict the chemical shift values of different ring structures having the same substituents. The PCA was used to demonstrate possible groupings of objects, and the PLS analysis was used to predict chemical shift values within the groupings.

As should be noted, none of the above techniques are designed to readily evaluate structural and functional similarity or diversity by identifying a substructure of an unknown compound; classifying membership of a compound in a family of compounds; analyzing a compound with respect to a computer generated model of a pharmacophore; or quantifying diversity or similarity within a set of compounds.

SUMMARY OF THE INVENTION

The present invention embodies both a method and apparatus for accomplishing molecular structure recognition by NMR spectral analysis using PCA to evaluate structural and functional similarity and diversity. Objectives of the invention are to determine whether a compound possesses a particular molecular substructure; to ascertain the complete molecular structure of a compound by uniting the identified substructures; to confirm membership (by inclusion or exclusion) of an unknown compound with respect to a group of closely related compounds, to predict whether a compound is likely to possess pharmaceutical activity by means of a specified pharmacophore; and to investigate the magnetic environment of a selected pharmacophoric target by analyzing diverse ligands thereof.

The first embodiment of the present invention facilitates the identification of a molecular substructure in an unknown compound by comparing NMR spectral data of a set of structurally related known molecules with that of a structurally related unknown. The entire structure of the unknown can be elucidated by analyzing discrete substructures until all substructures are identified. Substructures must contain excitable NMR-detectable nuclei to be analyzed by the present invention.

The second embodiment examines structural relationship of a specific molecule to a group of structurally related molecules in order to determine whether the specific molecule would or would not be a member of the group.

The third embodiment of the present invention intends analysis of a specific molecule with respect to pharmacophore possession by comparing NMR spectral data of a set of functionally related molecules with that of the specific molecule. These functionally related molecules are preferably compounds which are related to one another based on their similar binding affinity to a particular binding site.

The fourth embodiment of the present invention applies to analysis of a group of selected molecules to provide for a rapid and empirical assessment of structural diversity (similarity or dissimilarity) of a set of compounds. This embodiment is useful in certain combinatorial chemical synthetic efforts where structural diversity is a synthetic goal. This embodiment can be used to accurately measure the chemical diversity once the compounds are synthesized.

It is an objective of the present invention to quickly identify substructures in an unknown compound. As stated above, the first embodiment of the present invention permits the identification of substructures within an unknown compound by using conventional one-dimensional proton NMR data and an NMR database with known compounds containing the substructure of interest. The database is composed of a series of compounds having the common substructure. NMR data from the database is analyzed via PCA to create a PCA training data set referred to as a "model." The unknown compound data to be examined comprises the chemical shifts of the protons in the substructure in question. Permutations are generated for the chemical shifts of all of the unknown compound's hydrogen atoms to assure that all possible chemical shifts are compared to the model, and a PCA is performed on each possible hydrogen atom combination.

A PCA score plot is generated to compare the PCA scores of the training data set versus the PCA score of the unknown compound. PCA score plots are plots of two principal components for each testing compound and the unknown. The principal components are referred to herein as first principal component (t1 or tPS[1]), second principal component (t2 or tPS[2]), third principal component (t3 or tPS[3]) and so forth; the principal components are listed in order of decreasing significance. A PCA score plot may include first-third, first-fourth, second-third, second-fourth, components, etc. A compound which contains the substructure in question will be in the same PCA score plot region as the training set data points. By contrast, compounds without the substructure in question, despite similarities in chemical shifts, distribution and structure, will fall outside the PCA score plot.

The method of the first embodiment may be used in conjunction with combinatorial chemistry processes to provide automated NMR structural identification of newly synthesized compounds during high throughput synthesis thus affirming the incorporation of a desired substructure. It is preferred, in the case of high throughput analysis, to use one-dimensional $^1$H NMR spectral data to facilitate rapid identification. Furthermore, the analysis provided by this method of the invention can be repeated allowing the determination of all substructures within an unknown molecule (provided NMR-active nuclei are present in each substructure).

Another objective of the present invention is to provide a method for determining structure-based membership of a molecule in a family of molecules, or exclusion therefrom. The second embodiment of the present invention is a method which determines if an unknown compound belongs to a set of closely related compounds, or excludes the unknown from the set. The unknown sample is analyzed in the same manner as samples in the first embodiment except that no permutations are computed. Only the NMR signal intensities of the entire spectrum or a selected subset of the entire spectrum are treated. The model is compared to the PCA results of the entire spectrum of the unknown molecule, or a subset, without regard to specific chemical shift assignments per substructure. As will be recognized by persons skilled in the art, the first and second embodiments of the present invention provide molecular structure recognition techniques designed to identify or provide information regarding the structure of a molecule.

A further objective of the present invention is to provide a tool for investigating a pharmacophore. The present invention assists in the analysis of binding sites by creating a model based on a training set. The third embodiment of the present invention provides a method which permits the analysis of a pharmacophore by comparing the NMR spectral data of a training set of compounds which bind to a known receptor or have a common biological effect, with that of a test compound (the unknown). This embodiment compares structurally and non-structurally related compounds based on their affinity for a specified binding site to an unknown compound. This comparison permits prediction of the binding affinity of the suspect compound for the same site. In essence, an inverse spectral model of the binding site, manifested in the NMR spectral data and represented by the results of the described statistical analysis of the data, is generated. This third embodiment is a molecular function recognition technique which is designed to elucidate a molecular function (e.g., binding) instead of a molecular structure; however, a model of the interface structure of the binding site is generated.

Yet another objective of the present invention is to enable a quantitative description of diversity of a group of compounds. The fourth embodiment permits rapid and empirical assessment of structural diversity. The NMR spectrum of related and unrelated compounds and sets of compounds are compared. This embodiment assists combinatorial chemistry synthesis efforts where the goal is either constraining or expanding structural diversity of the resulting compounds.

These and other advantages of the present invention will become readily apparent upon further review of the following drawings and specification.

BRIEF DESCRIPTION OF THE DRAWINGS

The novel features of the described embodiments are specifically set forth in the appended claims; however, embodiments relating to the structure and process of making the present invention, may best be understood with reference to the following description and accompanying drawings.

FIG. 5 is an example of a positive test set according to the present invention wherein the compounds are referred to by an identification number and only the chemical shift vales for the corresponding protons in the substructure are listed.

FIG. 6 shows an example of a negative test set according to the present invention wherein the compounds are referred to by an identification number and only the chemical shift vales for the corresponding protons in the substructure are listed.

Similar reference characters denote corresponding features consistently throughout the attached drawings.

DETAILED DESCRIPTION OF PREFERRED EMBODIMENTS

The term "unknown" is used herein to refer to both (1) compounds with an unknown molecular structure and (2) other compounds having unknown structure/function memberships whether or not the structure of the compound is known. The unknown compounds are organic compounds having NMR-active nuclei. The term "organic molecule" or "organic compound" as used herein refers to an entire range of compounds comprised of small organic molecules to macromolecules.

I. Sub-Structure Analysis

The method of the present invention may be used to identify structurally related compounds and structurally diverse compounds having a substructure in common. In other words, the method allows determination of whether a specific substructure is present in an unknown compound. The first embodiment of the present invention is illustrated in the flowchart of FIG. 1.

Initially a training set of compounds is assembled. The term "training set", as used herein, refers to a group of compounds each containing a structural or spectral pattern of interest which is used to define a PCA generated model. A more detailed mathematical description of PCA is provided in the Appendix, infra. The training set 112 of this embodiment, as shown in FIG. 1, preferably consists of a family of structurally related compounds, wherein each compound contains the substructure in question. A training set which comprises structurally diverse compounds containing the substructure in question may also be used in place of a family of structurally related compounds; however, a larger number of structurally diverse compounds would normally be required to reliably identify an unknown compound than would be required to identify a structurally related unknown compound from a PCA generated model using a family of structurally related compounds.

NMR spectral data (shown 114) is collected for each compound in the training set. NMR chemical shift data for NMR-active nuclei are used primarily in the present invention. The use of one-dimensional high field hydrogen-1 NMR spectroscopy is preferred; however, other 1-dimensional NMR spectroscopy using other NMR-active nuclei, such as carbon-13 or nitrogen-15, may be used. In addition to primary chemical shift data, other NMR data, such as spin-lattice and spin-spin relaxation rates, scalar and dipolar coupling patterns, Nuclear Overhauser Effect (NOE) signals, can also find use. For high throughput analysis, the faster one-dimensional high field hydrogen-1 NMR is most preferred; however, 2-dimensional and 3-dimensional NMR spectroscopy may also be used.

Figure 1:
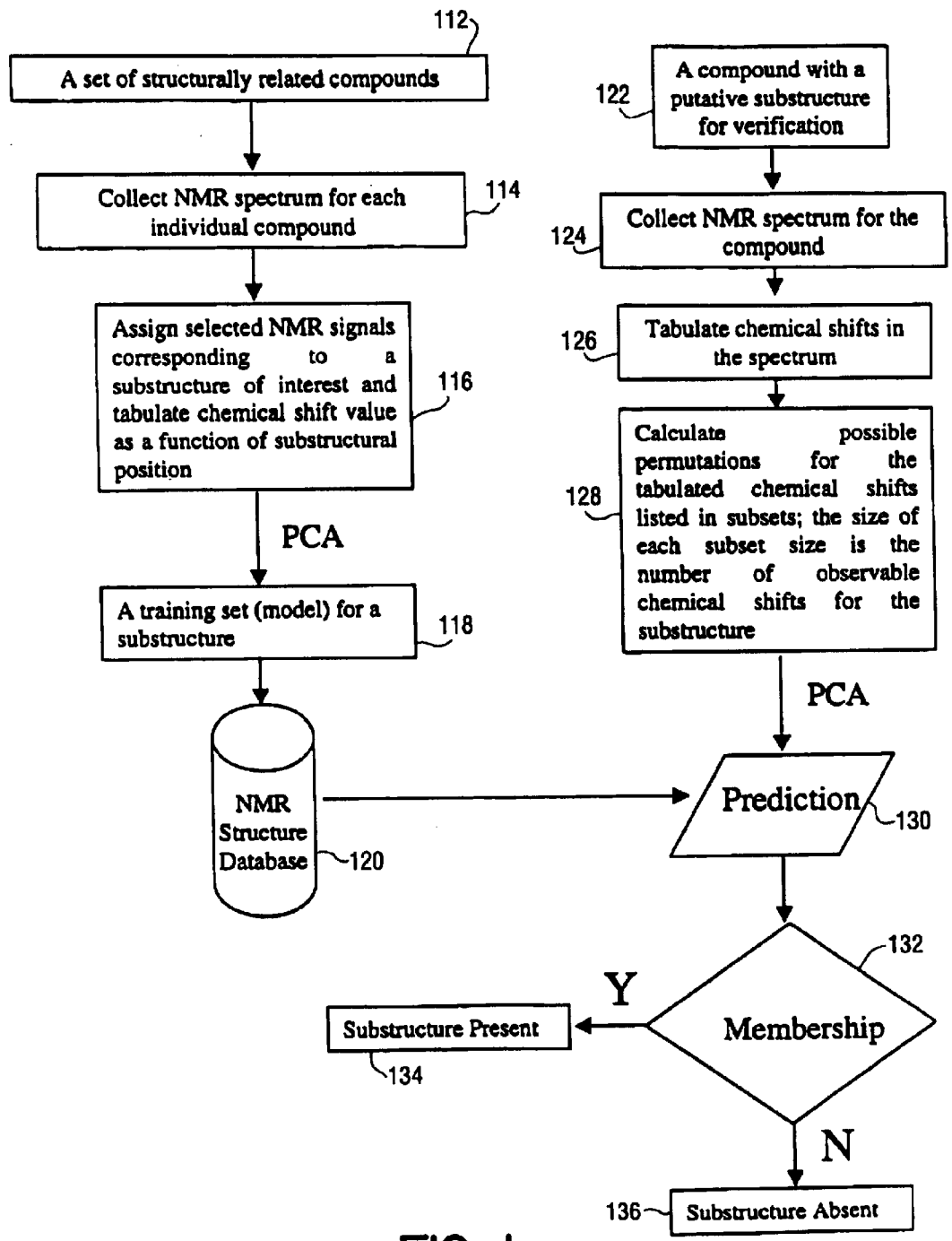
FIG. 1 is a flowchart illustrating a first embodiment of the present invention.

Selected NMR signal data are assigned corresponding to the substructure of interest, and the chemical shift values are tabulated as a function of the position of the substructure in the molecule (as denoted by 116 in FIG. 1). The numerical value of a nuclei's chemical shift in parts per million (ppm) is preferably used, and is conventionally defined as:

$$\delta = \frac{\omega_{signal} - \omega_{referencel}}{\omega_{referencel}} \times 10^6;$$

where δ (represents the chemical shift value, $\omega_{signal}$ represents the frequency of the chemical shift signal of the compound tested, and $\omega_{reference}$ represents the frequency of a reference compound. The unit parts per million (ppm) is used instead of Hz because ppm units are independent of the magnetic field strength. In this embodiment of the instant method, the intensity of the chemical shift signals is irrelevant.

From these chemical shift values, a first set of principal components of the chemical shifts for nuclei found in the substructure of each of the structurally related compounds is calculated forming a "training set," or model (shown as 118 in FIG. 1), for the substructure of interest. The first set of principal components corresponds to the chemical shifts of the active nuclei of the substructure only, and those of other active nuclei which are not part of the substructure are not included. PCA is a well known data reduction method, known to one skilled in the art, using mathematical techniques to identify patterns in a data matrix. The main element of this approach consists of the construction of a small set of new orthogonal, i.e., non-correlated and independent, variables derived from a linear combination of the original variables. A concomitant reduction in the number of variables results from PCA analysis. Numerous software programs are available to perform PCA such as the Simca-P 8.0 software package from Umetrics or JMP V.3.2.6, Statistical Discovery Software.

An NMR structure database (120 in FIG. 1) may be established to contain a plurality of models. The models are each drawn to separate substructures. Although each model corresponds to a separate substructure, more than one model may be drawn to the same substructure. In other words, each model may contain a family of closely related compounds having the substructure in question. Alternatively, a single model for the substructure in question may be generated which contains structurally diverse compounds. When structurally diverse compounds are used to generate the model in question, statistical reliability is increased when many more compounds are included in the training set to provide a larger pool of chemical shift data corresponding to the substructure than when structurally related compounds are used. A test set comprised of selected compounds may be used to validate the model. The term "test set" refers to a group of known compounds which may or may not have the structural or spectral pattern of interest. The test set is used to determine accuracy of the PCA model resulting from the training set. Only a validated model with a desired level of accuracy and reliability is to be used for determining a specific substructure in an unknown compound.

In FIG. 1, an unknown compound (122) is to be tested. The unknown compound may or may not have the substructure in question. For compounds generated by high throughput synthesis, the presence of the expected substructure in a newly synthesized compound can be confirmed by application of the present method. For greater accuracy and reliability in confirming the presence of a desired substructure, it is preferable to employ a model (118) comprised of structurally related compounds which would be expected to be similarly related to the compound of interest. When no structural information is available for the unknown compound, it is preferable to use either a model of structurally diverse compounds or a plurality of models of structurally related compounds having the expected substructure in question, each model differing structurally from the other models.

An NMR spectrum (124) is recorded for the unknown compound and may be a one, two or three-dimensional NMR of the NMR active nuclei found in the unknown compound. The comparative NMR data must be of the same type for both the model and the unknown. For high throughput NMR spectroscopy; e.g. as applied to combinatorial chemistry, it is most preferred that the spectrum be a one-dimensional $^1$H NMR spectrum.

As shown in FIG. 1, the chemical shifts in the spectrum are recorded (126) and all possible permutations for the chemical shifts are generated (128). A permutation (nPr) is an ordered subset (i.e., attention is paid to the order of selection or arrangement) of a particular set of objects. If the set consists of n objects, r such objects can be selected to give n!/(n−r)! permutations. In the present embodiment, the n represents the total number of chemical shifts determined by the NMR spectrum (of the unknown), and r represents the total number of chemical shifts (of the NMR-active nuclei) found in the substructure in question. The chemical shift permutations are then listed in an [n!/(n−r)!]×r matrix, or fitted into an [n!/(n−r)!]×r spreadsheet. In practice, the number of permutations to be calculated and included for analysis can be significantly reduced by confining the calculation to the chemical shifts that have similar values with the chemical shifts used in the model.

PCA is performed on each set of the chemical shifts in the matrix or spreadsheet. A second set of principal components is calculated composed of principal components for each permutation. This set of principal components is compared to the first set of principal components of the PCA-model to determine PCA-based membership, as denoted by "Prediction" (130). In some instances, the first two principal components only account for less than a desired percentage (e.g. 90%) of the variances of the data. In that case higher order principal components (such as the second, third, and fourth principal components) are needed to make meaningful distinctions between the training set (model) and the testing (unknown) data sets as illustrated in following examples infra. Whether any member of the second set of principal components is clustered with the first set of principal components is determined by statistical comparison means, as denoted by "Membership" (132).

If the substructure is present (134), then the PCA score will be clustered with the training set. If the PCA score is not clustered with the training set then the substructure absent (136) from the unknown compound. In these appliations of the present method, clustering has been performed and represented by a statistical comparison means, T2 Hotelling Ellipse. The data clustering or comparison may also be achieved by other algorithms, similar to or different from the PCA-based approach, such as Mahalanobis Distance, Heirarchical Clustering, and Mutually Exclusive analyses. One skilled in statistical analysis of data would be familiar with these and alternate means for use in the instant invention.

Substantive analysis may be repeated for each potential substructure until all substructures having NMR-active nuclei are identified, provided a model for each potential substructure is available. It is desirable to use more than one type of NMR spectral data for the complete elucidation of a unknown structure. Other types of spectral data that may be used include one-, two-, and three-dimensional (homo- and hetero-nuclear) data for hydrogen-1, carbon-13, nitrogen-15 and phosphorus-31 nuclei. Additionally, data pertaining to relaxation rates, coupling patterns, and NOE may also be employed.

An apparatus for identifying a substructure of an unknown organic compound comprising a spectrometer means for collecting NMR spectral measurements, a computer means for compiling and analyzing the data, and an output means for displaying the analysis results is also contemplated by the present invention.

Application of this analytic method will be illustrated by means of the following examples describing the process of using the method to identify substructures in unknown compounds. These examples are in no way intended to limit use of the inventive method in its applications.

EXAMPLE 1

In this example, a commercial database was used as the source for the NMR data in the training set. The PCA modeling was performed with the Simca-P 8.0 software package from Umetrics. Substructures and the corresponding chemical shift values were taken from the ACD $^1$H NMR database from the Advanced Chemistry Development 4.04. Microsoft Excel 97 was used for managing the data sets and data output.

Figure 4:
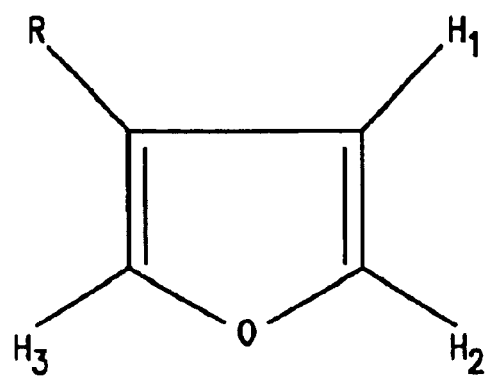
FIG. 4 shows a furan ring substructure.

The substructure in this example was a furan ring with a substituted group denoted as R, as shown in FIG. 4. The chemical shift assignments used were those of the protons on the unsubstituted positions of the furan ring. The chemical shift values of these three protons from various compounds are the selected data points comprising the data sets. The compound identification numbers and chemical shift values for the three protons corresponding to the substructure of interest make up a positive data test set (shown in FIG. 5). As shown, FIG. 5 is a table listing chemical shifts for a positive test set, that is, a test set having the required substructure. These chemical shifts correspond to the chemical shift values of the NMR-active nuclei (protons) in the substructure.

A negative test set is formed by including in the training set compounds that do not have the furan structure yet have chemical shift values and distributions similar to those of the compounds with the substructure. For each compound, its corresponding chemical shifts are listed and sorted in Excel.

To place chemical shift values into three proton positions (H1, H2, H3), corresponding to the protons in the substructure, permutations are calculated for chemical shift values for each compound test set using a permutation calculator. The permutations corresponding to the closest chemical shift values for the negative test set are listed in FIG. 6. All the permutations were used in the analysis. From a negative test set of 61 compounds, 6000 permutations resulted. Any permutation could theoretically be "the correct" one; if any permutation has a positive identification, the entire compound is considered positive.

Figure 7:
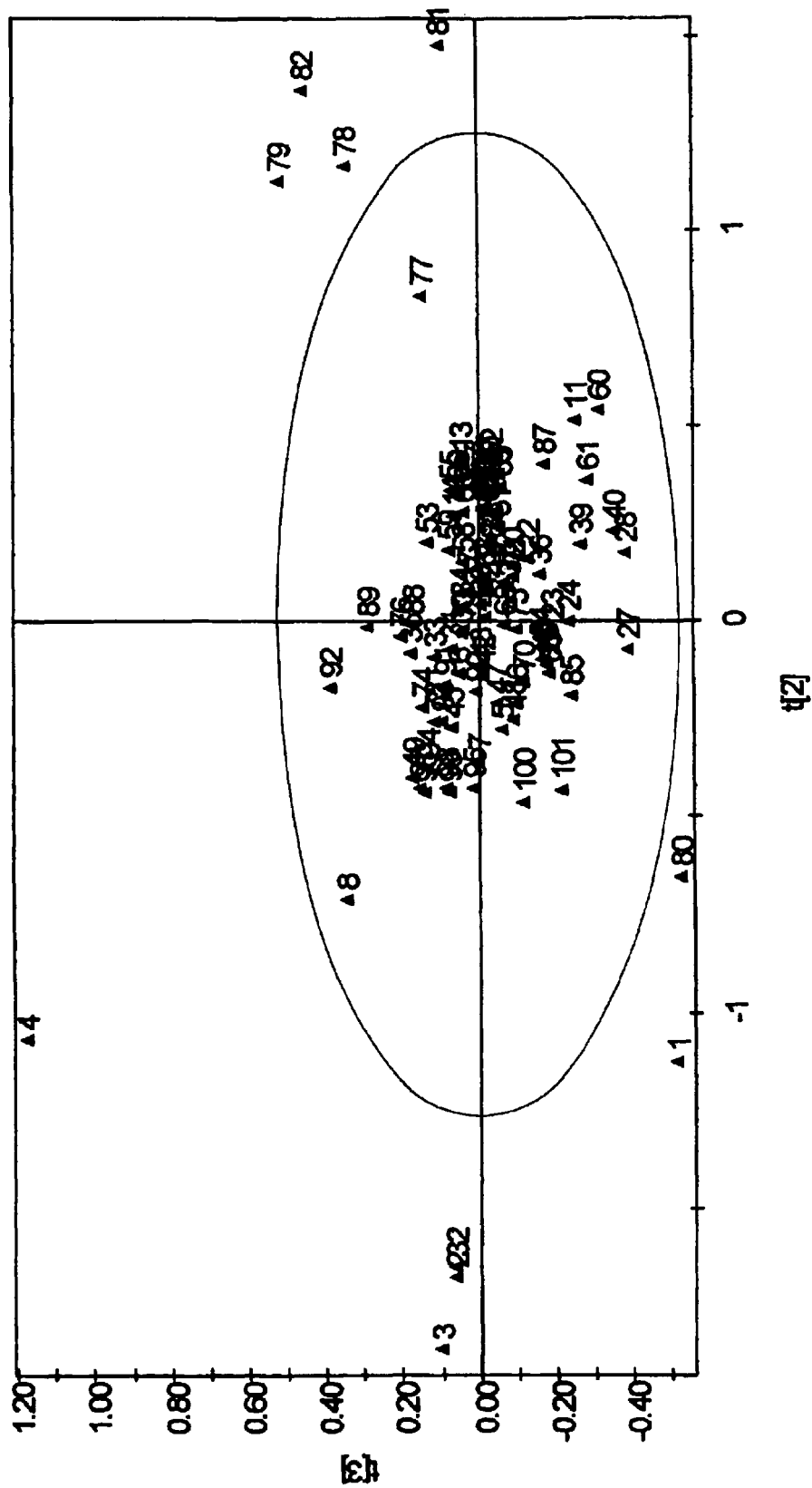
FIG. 7 represents a typical score scatter plot wherein any data point which falls outside of the ellipse is considered an outlier based on t(2) versus t(3) analysis.

A training set comprised only of compounds containing the specified substructure; e.g., a furan ring, can be constructed by selecting compounds for the training set in one of two ways. The first way (used in the present example) is to choose clusters of data points from the t2/t3 score scatter plot generated in Simca, as shown in FIG. 7. After PCA is performed, a score plot is generated grouping compounds according to similarities. Choosing a related cluster from the scatter plot would decrease the number of compounds selected for the training set and would also decrease the variability in the structures.

The second way, not shown, is to use the probability of membership from a prediction sheet also generated in Simca. Originally, all the positive compounds would be included in the first iteration. When the spreadsheet is obtained, any compound with a probability below a selected value is excluded for the next iteration, and continuing until the desired probability for class membership is obtained for all the compounds in the training set.

To test the accuracy of the model, a group of compounds containing the furan ring were split in half, so that part became the training set, and part became the test set. For example, given a set of 101 positive compounds, 51 of these could be used as a training set, and 50 could be used as a positive test set. Alternatively, instead of splitting the group, one compound could be excluded at a time as a test set. If the training set of 51 were to be designated as a test set, PCA would be performed 51 times—one for the exclusion of each compound separately.

Figure 12:
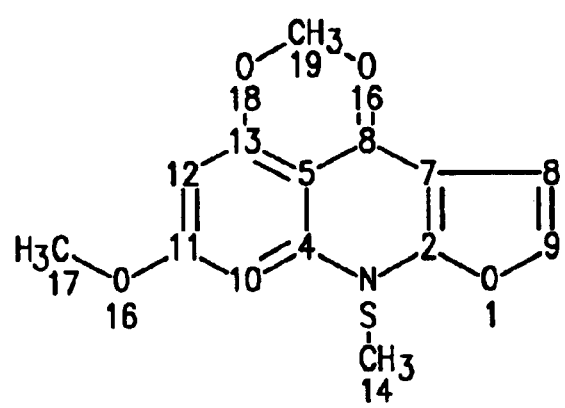
FIG. 12 shows a compound structure, designated 14267, which has the substructure shown in FIG. 4 as part of a fused ring structure.
Figure 8:
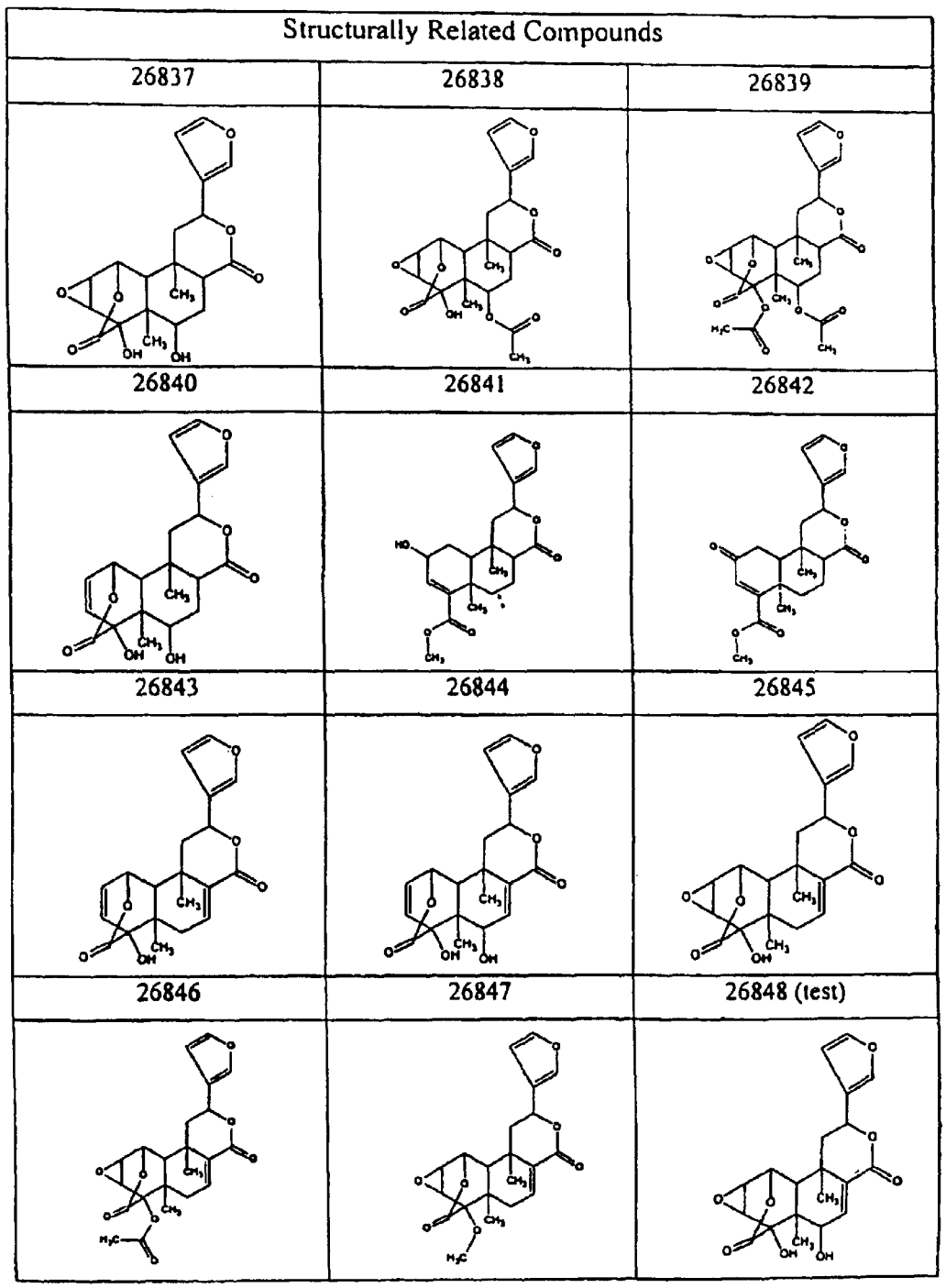
FIG. 8 is a table containing eleven structurally related compounds each having an appended furan ring and one related test compound.
Figure 9:
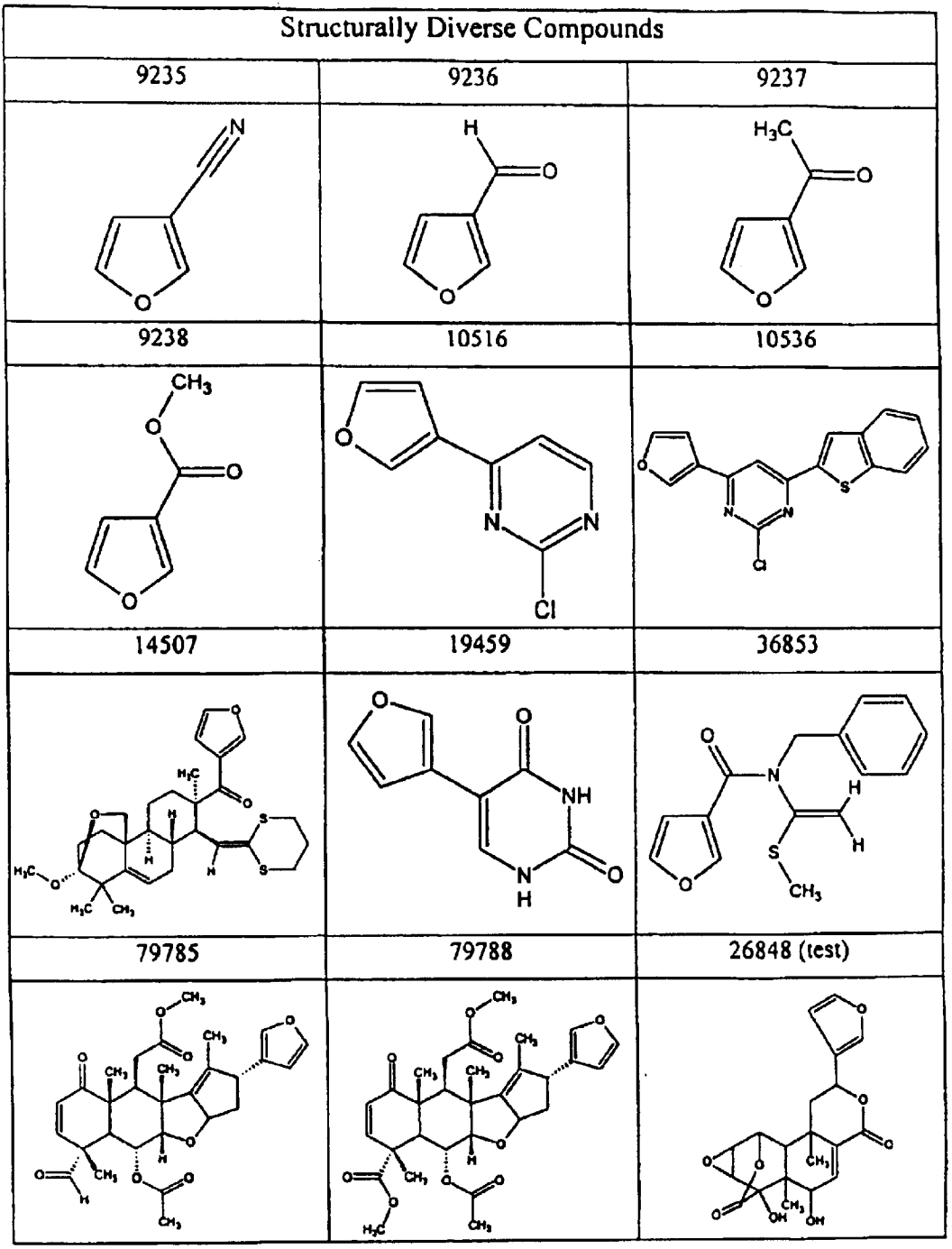
FIG. 9 is a table containing eleven structurally diverse compounds each having an appended furan ring and one test compound.
Figure 10:
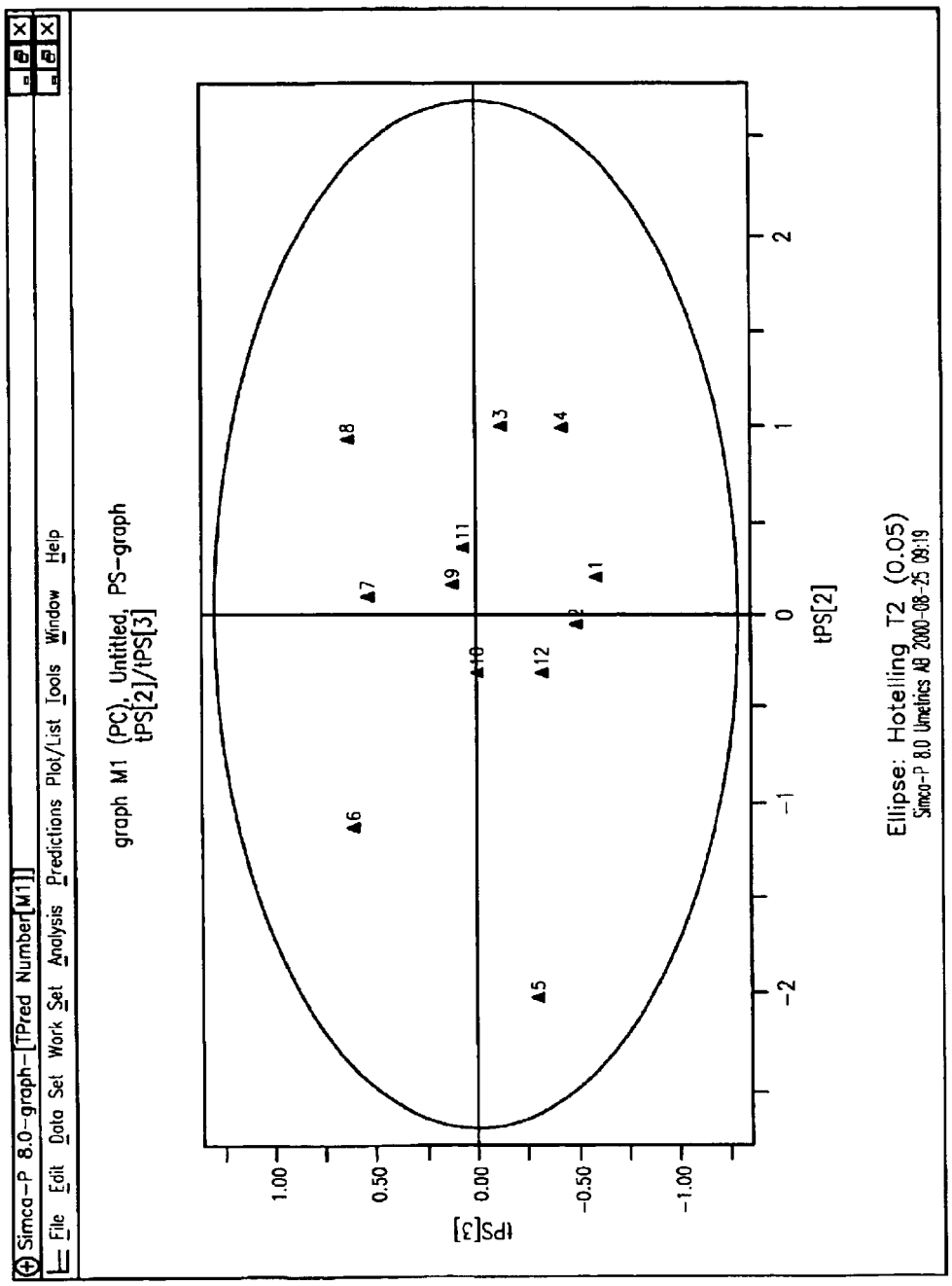
FIG. 10 is a score scatter plot of the principal components corresponding to the structurally related compounds and the test compound of FIG. 8.
Figure 11:
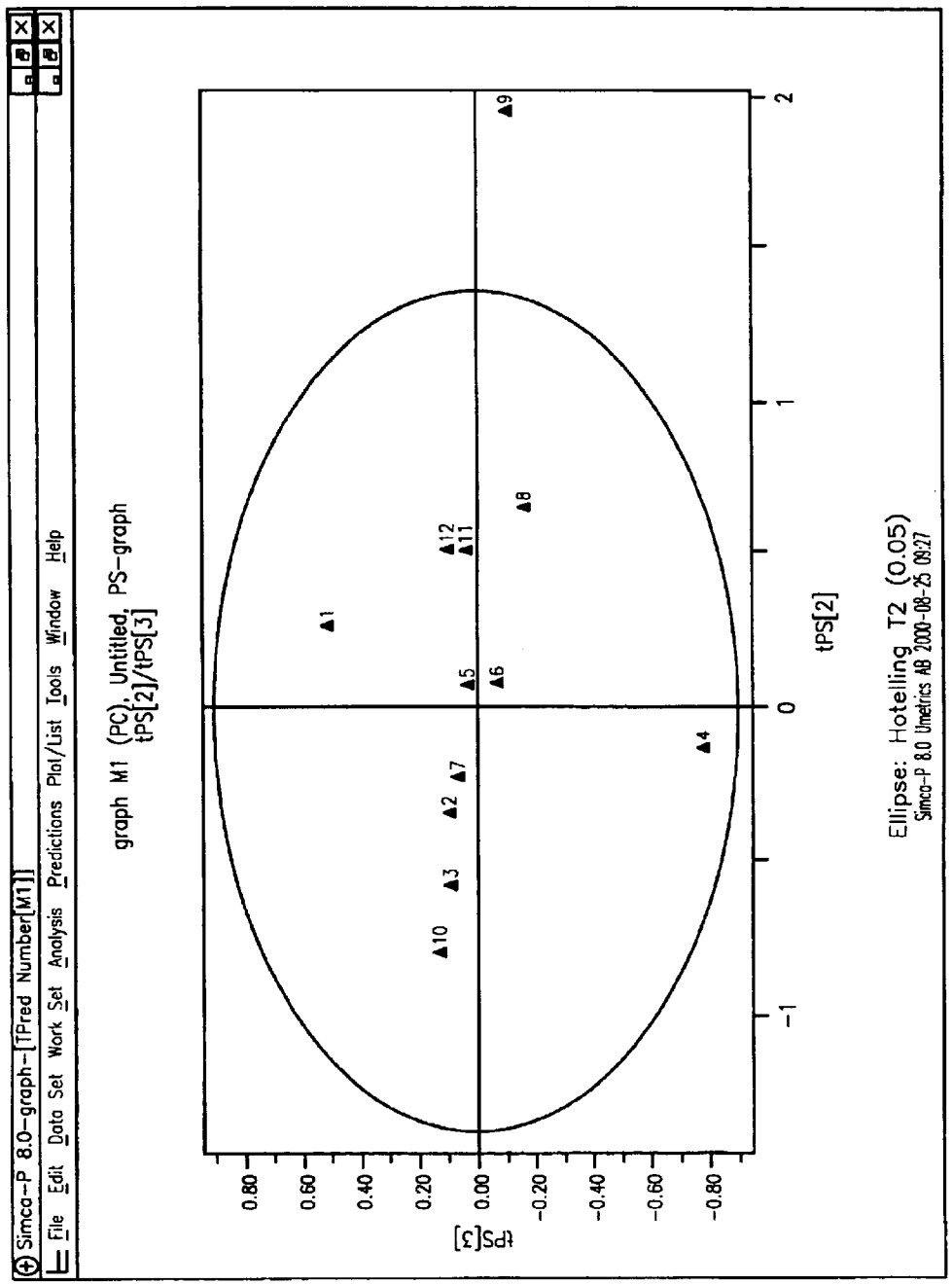
FIG. 11 is a score scatter plot of the principal components corresponding to the structurally diverse compounds and the test compound of FIG. 9.
Figure 13:
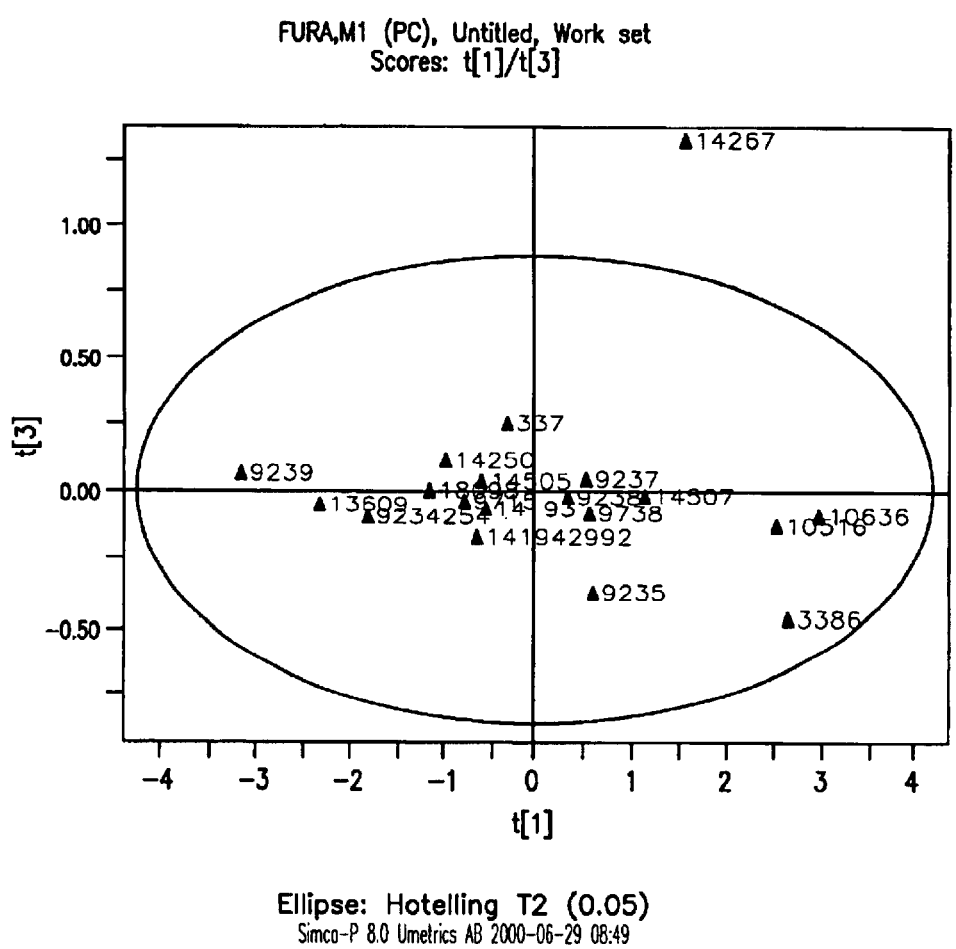
FIG. 13 is a scatter plot indicating that the fused ring compound shown in FIG. 12 is an outlier.

Two training sets were obtained; each comprised of 11 furan-containing compounds, shown in FIGS. 8 and 9. One training set was composed of structurally related compounds, shown in FIG. 8, whereas the other was composed of structurally diverse/unrelated compounds, shown in FIG. 9. The scatter plots shown in FIGS. 10 and 11 correspond to the structures shown in FIGS. 8 and 9, respectively. FIG. 10 shows a positive result for the test compound which is designated 26848 and labeled 12 on the plot. The chemical shift values analyzed in FIG. 10 are those listed in FIG. 5. The test compound (the unknown) is depicted within the ellipse indicating a positive result. FIG. 11 shows a false negative result for the same test compound, labeled 9 on the plot, which lies outside of the ellipse (an outlier) when analyzed with the structurally diverse compounds. This false negative result indicates the need for a larger number of compounds in the structurally diverse sample. These scatter plots are plots of the second and third principal components along the x- and y-axis respectively. The structure shown in FIG. 12, designated 14267 in FIG. 13, was analyzed and determined to be an outlier in the scatter plot shown in FIG. 13. The chemical shift values analyzed in FIG. 11 are shown in FIG. 6.

Generally, comparison of higher order principal component scores engenders the greater sensitivity of the model to variations in the structures of the test compounds versus the training set.

EXAMPLE 2

Figures 14, 15:
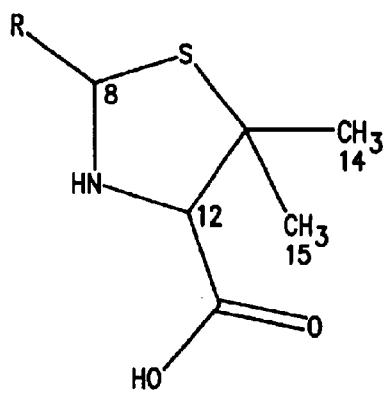
FIG. 14 shows a core structure common to many penicillins.
FIG. 15 shows a table of the chemical shift values of certain hydrogen atoms on the core structure of FIG. 14.

The components and methodology utilized in this example are similar to example 1. The substructure that was of interest in this example, shown in FIG. 14, is a basic structural component found in many penicillins. A training set of six compounds and a testing set of twelve compounds were analyzed. FIG. 15 shows a table of the chemical shift values for the pertinent protons. Entries 1–6 correspond to the training set, and numerals 7–18 correspond to the testing set.

Figure 16:
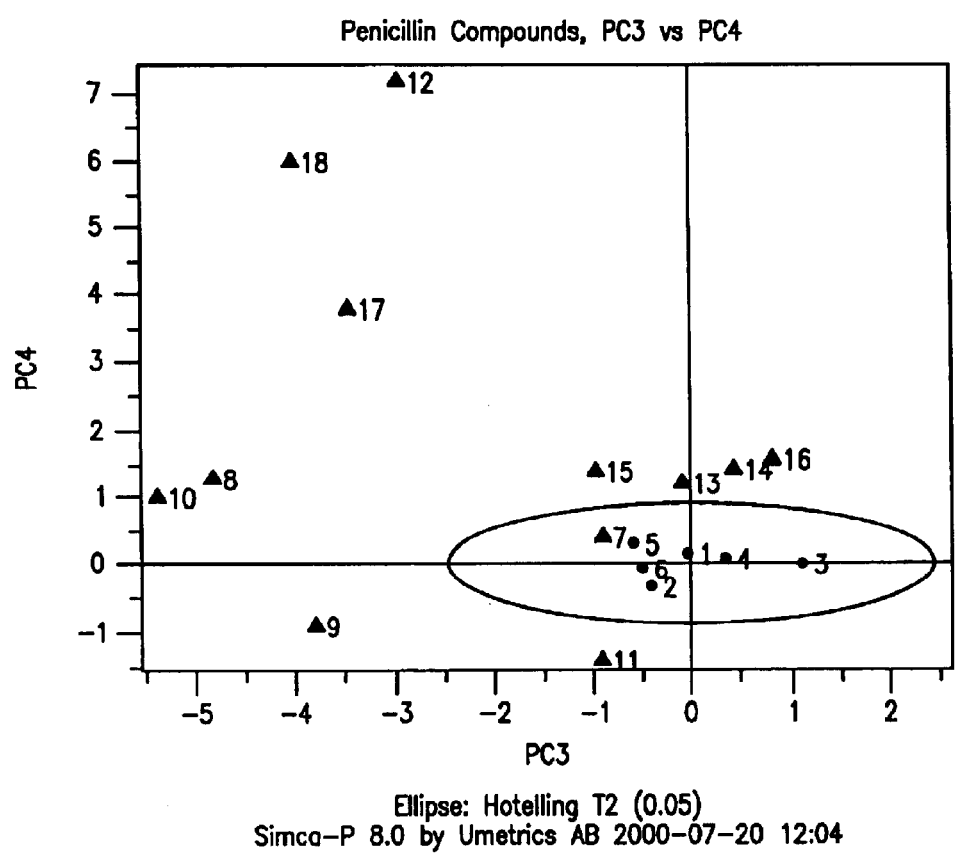
FIG. 16 is a scatter plot of the chemical shift values of FIG. 15.

FIG. 16 is a third/fourth principal component score plot. The plot shows that the training set used indicates that compound 7 (ID 36127) being within the elipse possesses the substructure while outlying compounds are those without the substructure. These outlying compounds (8–18) were outside the 95% confidence of the T2 Hotelling Ellipse shown in FIG. 16. This example demonstrates that for a series of drug analogs, as few as six training compounds can be used to make up the training set and effectively define a substructure of interest.

Figure 17A:
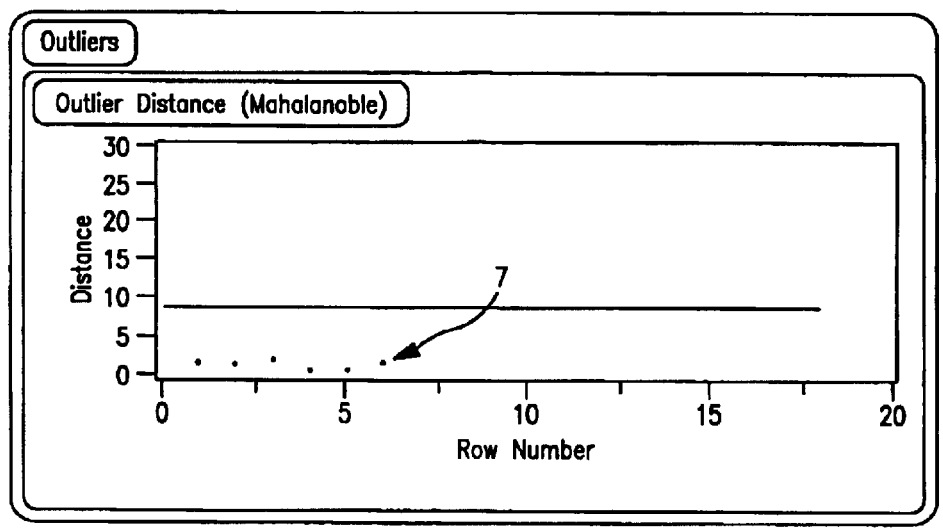
FIG. 17a is a Mahalanobis Distance plot showing the distance from each data point to the center of the multivariate mean, and indicating a compound having the substructure in common with the training set.
Figure 17B:
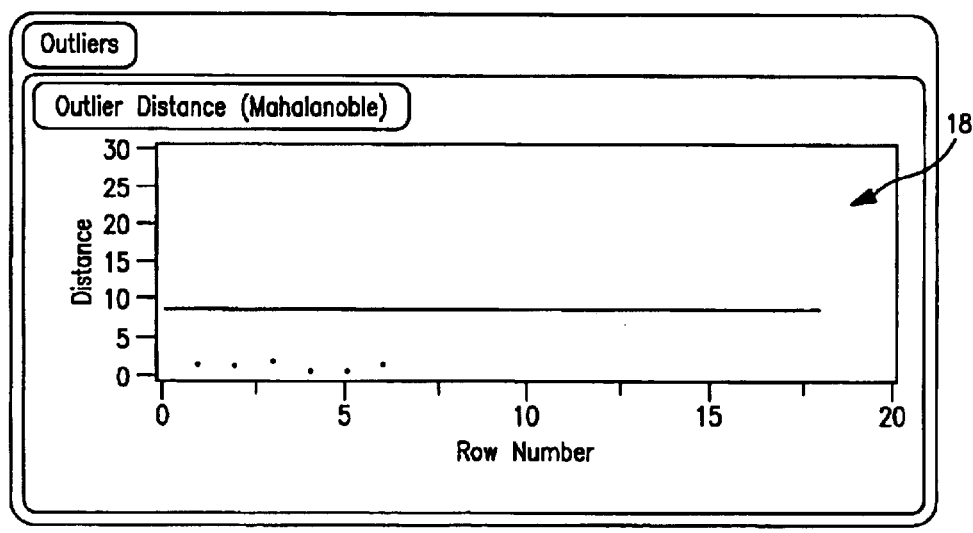
FIG. 17b is a Mahalanobis Distance plot showing the distance from each data point to the center of the multivariate mean, and indicating an outlier.

Other statistical approaches for outlier identification and data classification can also be used. FIGS. 17*a* and *b* depict an alternative approach. A Mahalanobis Distance plot shows the distance from each data point to the center of the multivariate mean (or centroid). In this case, Compound 7 is correctly grouped along with the compounds in the training set, as shown in FIG. 17*a*. The outlier compound 18, in FIG. 17*b*, appears as a point with the largest distance values.

Other techniques which may be used include, the Heirarchical Clustering Method and Mutually Exclusive Models. Not only can the clustering method be used to predict outliers, it may also be used to establish a hierarchy of relatedness. In the mutually exclusive model, two clusters of compounds are generated. One cluster corresponds to the structures having the substructure and the other corresponds to excluded compounds which do not have the substructure in question. Both of these techniques accurately predict the outliers.

II. Membership of Unknown in a Group of Compounds

The method of the present invention may also be used to classify compounds; e.g., identify whether an unknown compound belongs to a group of structurally related compounds. In other words, the invention allows determination of membership of an unknown compound in a group of closely related compounds. The second embodiment of the present invention is illustrated in the flowchart of FIG. 2.

Figure 2:
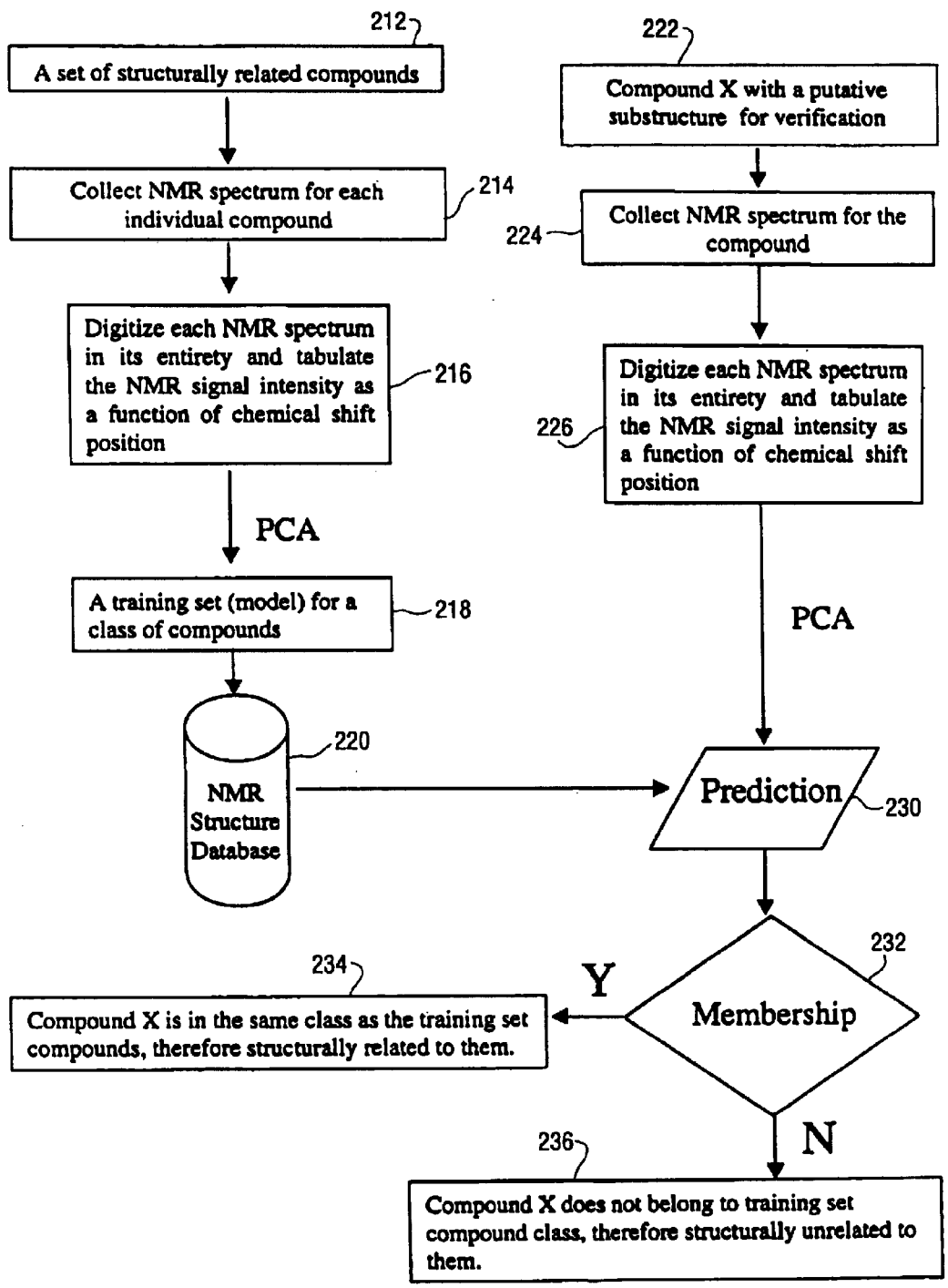
FIG. 2 is a flowchart illustrating a second embodiment of the present invention.

Initially a training set of compounds is assembled and, in this application, consists of a family of structurally related compounds, (denoted by 212 in FIG. 2).

NMR spectral data is collected (214) for each compound in the training set. NMR chemical shift data for active nuclei are used. The use of 1-dimensional high field hydrogen-1 NMR spectroscopy is preferred, as in the previous embodiment, however other 1-dimensional NMR spectroscopy using other NMR-active nuclei, such as carbon-13 or nitrogen-15, may be used. Also, 2- and 3-dimensional NMR spectroscopy may be used.

Each NMR spectrum data is converted from its original binary format into the ASCII or text format, a process herein referred to as "digitization," according to a procedure further detailed below; the signal intensity is tabulated as a function of chemical shift position (216). Either the entire spectrum or a subset of the spectrum corresponding to structures of interest are used. From these tabulated values, a first set of principal components of the signal intensities of the chemical shifts for nuclei found in each of the structurally related compounds is calculated forming the training set (model) (218) for the family of compounds of interest. As before, the first set of principal components corresponds to the NMR-active nuclei in the training set. An NMR structure database (220) may be established to contain a plurality of models. The models are each drawn to a separate family of compounds.

An unknown test compound (compound X, 222) is selected which may or may not belong to the family of compounds in question. The term "unknown" is used to refer to any compound tested, and need not be an actual unknown.

An NMR spectrum of the unknown test compound is collected (224). The NMR spectrum may be one-, two- or three-dimensional NMR of any NMR-active nuclei found in the unknown compound. The NMR data is the same type for both the model and for the unknown, and is preferably generated using the same reference compound. Each NMR spectrum is digitized in its entirety and the NMR signal intensity is tabulated as a function of chemical shift position (226). Alternatively, discrete sub-regions of the spectrums (training set and unknown) may be digitized and used.

The approach using the entire spectrum correctly distinguishes compounds with and without a common core structure. This approach also distinguishes structurally similar compounds into related subclasses. The alternate approach examines a subset or subsets of the NMR spectra where the most relevant structural variability is expected to occur.

PCA is performed on the digitized data. A second set of principal components is calculated composed of principal components in tabulated form. The second set of principal components is compared to the first set of principal components to determine PCA-based membership, as shown as "Prediction" (230). Again, higher order principal components are used, as before. Whether any member of the second set of principal components is clustered with the first set of principal components is determined by statistical comparison means, shown as "Membership" (232). The same statistical comparison means may be used in this embodiment as in the first embodiment.

If the substructure is present (234), then the PCA score will be clustered with the training set. If the PCA score is not clustered with the training set then the unknown compound is not a member of the family of closely related compounds (236). The clustering is performed by a statistical comparison means such as T2 Hotelling Ellipse, Mahalanobis Distance, Heirarchical Clustering, and Mutually Exclusive analyses.

An apparatus for identifying membership of an unknown compound in a family of compounds which includes a spectrometer means for collecting NMR spectral measurements, a computer means for compiling, collating and analyzing the data, and an output means for displaying the results is also contemplated by the present invention.

The model validation considerations of the second embodiment are the same as in the first embodiment. The details of this analysis will be made clearer by means of the following two examples.

EXAMPLE 3

Thirty eight compounds were used in this example. Twenty-one compounds are designated as Class I compounds and are referred to by the numbers 1 through 21 on the plots shown as FIGS. 18 and 19. The Class I compounds were obtained from a combinatorial library and share a core structure. The remaining compounds, referred to as Class II compounds, were randomly selected and lack the core structure. The Class II compounds are referred to by the numbers 22 through 38. Five of the Class I compounds (8, 10, 14, 17, and 19) were used as the training set.

Following synthesis of the Class I compounds, a 50–100 $\mu g$ sample of each was dissolved in 60 $\mu l$ DMSO-$d_6$ solution. The solution was immediately transferred into a Wilmad 1.7 mm OD capillary tube (WG-1364-1.7). The tube was then flamed-sealed to prevent moisture collection and solvent evaporation. The one-dimensional 1H NMR data were collected for each of the Class I compounds under identical experimental conditions in DMSO-$d_6$ at room temperature. All one-dimensional standard $^1$H NMR data were collected on a Varian 500 MHz Inova Unity system in a Nalorac submicro-probe (SMITG-1.7). A total of 64 to 128 scans were used, depending on the actual sample concentration. No window functions were applied and minimal shimming was performed between samples.

The NMR data for each compound was further "digitized" prior to PCA by first dividing a full processed spectrum into a series of 5 Hz wide fine regions. Each region serves as a variable for the compound. A single compound can therefore be described by up to 1000 such variables (10 ppm×500/5= 1000). The data from 10 to 0 ppm were extracted and submitted to PCA. All input variable values for each spectrum were normalized with respect to the total integrals.

PCA was completed using Simca-P 8.0 software (Umetrix AB). The spectral "digitization" and Varian-to-Simca data format conversion include the following steps and are automated by a series of the Varian Magical-based macros and Unix scripts. Macros were used to sequentially process all FID files, defined in a file, and to divide each spectrum into 5 Hz wide grids based on a given spectral range. The resulting text files, each a single-column data list with integral values for all the grids in a spectrum, were then merged into a single data file using a UNIX script. The file is then directly read into Simca, transposed so that each column represents the same grid position in all the original spectra and each row contains all the integral values across the specified spectral region for a compound.

Figure 18:
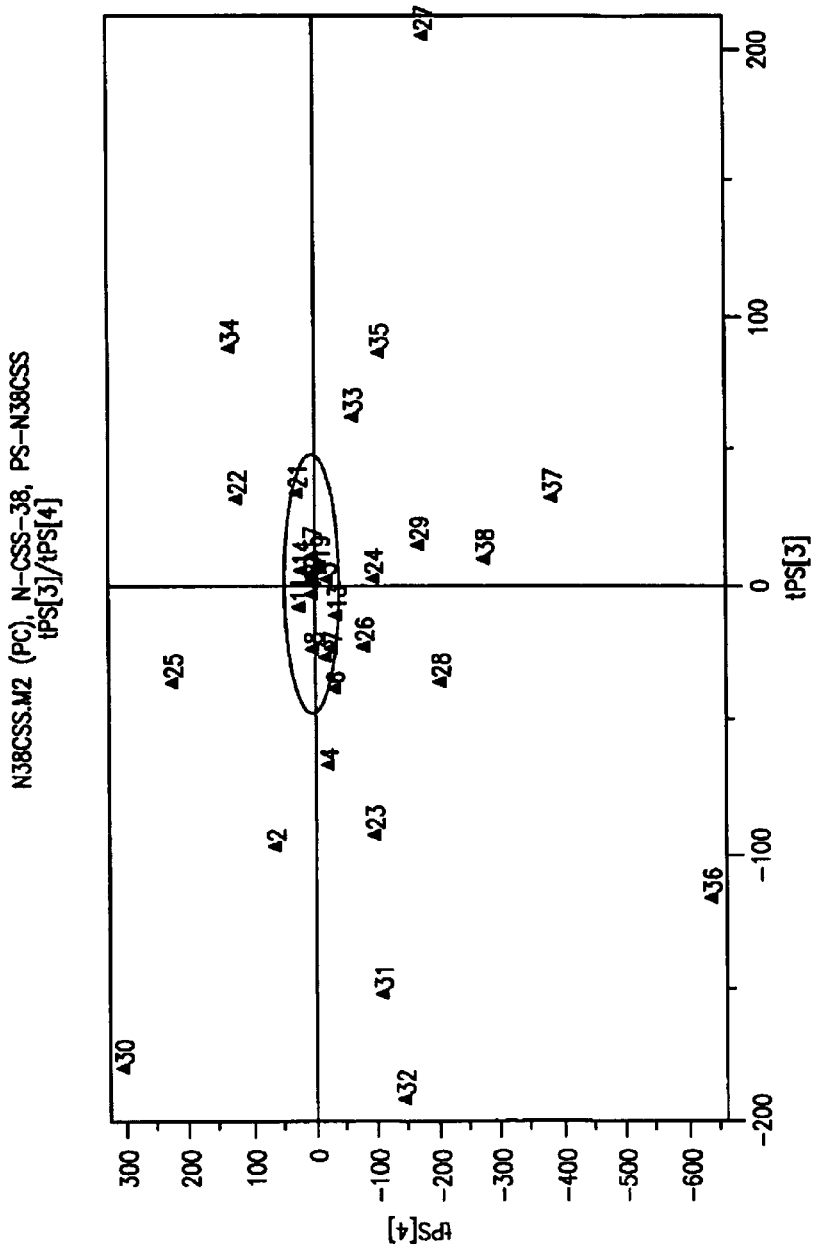
FIG. 18 is a scatter plot indicating the outlying compounds in example 3.
Figure 19:
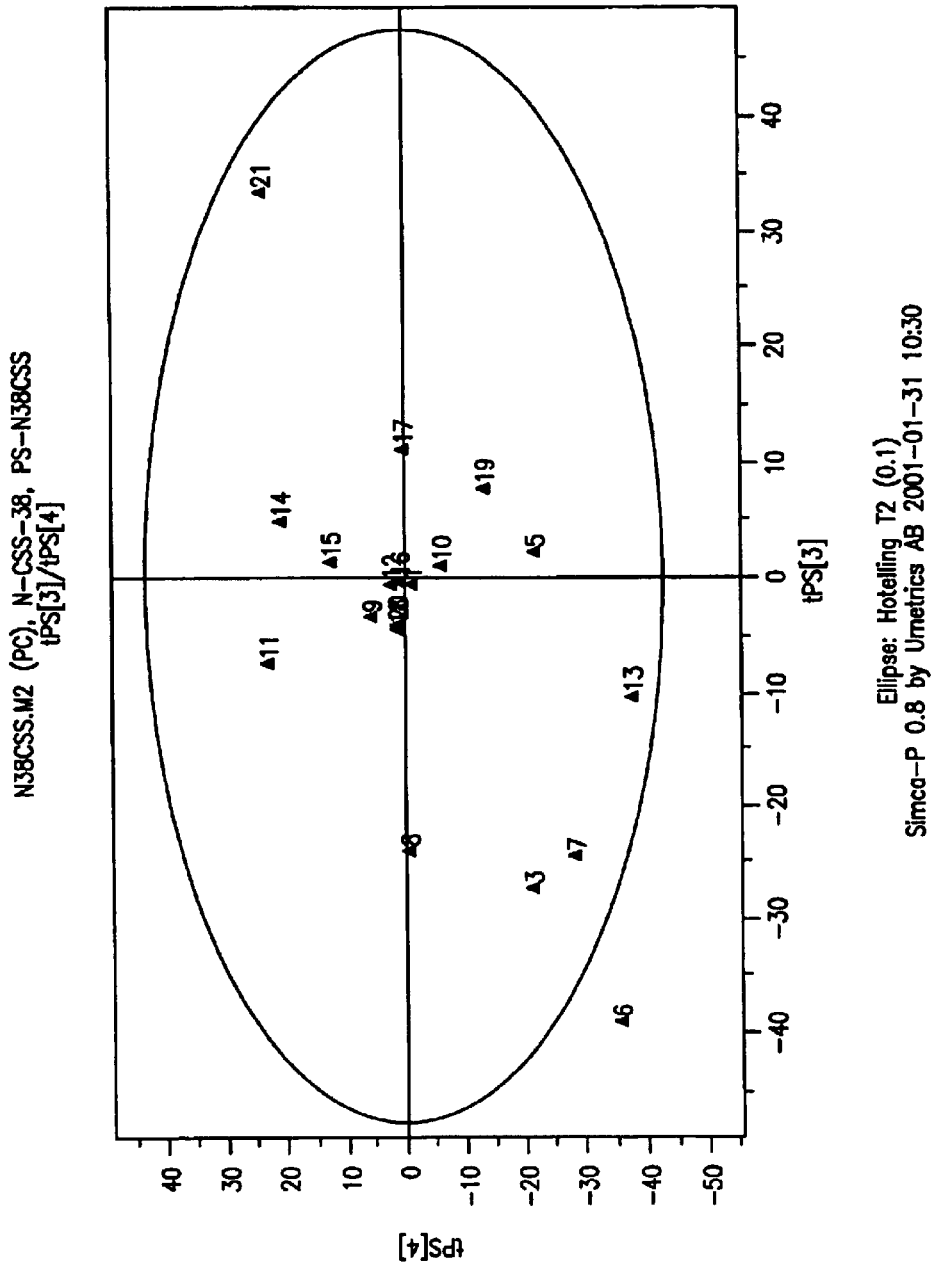
FIG. 19 is a scatter plot indicating compounds belonging to the family of structures in example 3.

The resulting data were plotted and are shown in FIGS. 18 and 19. FIG. 18 clearly shows that the compounds in Class II are outliers. FIG. 19 is a closer view of the ellipse in the center FIG. 18 and shows that the majority of Class I compounds are included within the ellipse indicating membership in the family of compounds with no less than 90% confidence.

EXAMPLE 4

The analytic procedures in this example are similar to those described in Example 3. In this case, the Class I compounds were further subdivided into Class IA and Class IB. Class IA refers to compounds 1 and 8 through 21 and have an additional common substructure. Class IB compounds are designated by the numbers 2 through 7. The selected part of the processed spectrum was divided into a series of 5 Hz wide fine regions. Also, only the data in regions 7.4–6.8 ppm, 4.0–3.6 ppm, and 3.2–1.4 ppm were used in the PCA. These regions are most characteristic of the signals arising from the core structure and from the additional substructure. In regard to the PCA, the macros were used to sequentially process all FID files, defined in a file, as before. Each spectrum was "digitized" into a series of 5-HZ wide grids based on the spectral ranges indicated, as before.

This alternate approach not only accurately recognizes non-Class I compounds but also further distinguishes Class IA from Class IB compounds. Furthermore, this approach is very useful for rapid analysis of structurally similar compounds, particularly in the combinatorial chemistry setting or in drug stability studies when only minor structural changes have been made.

Figure 20:
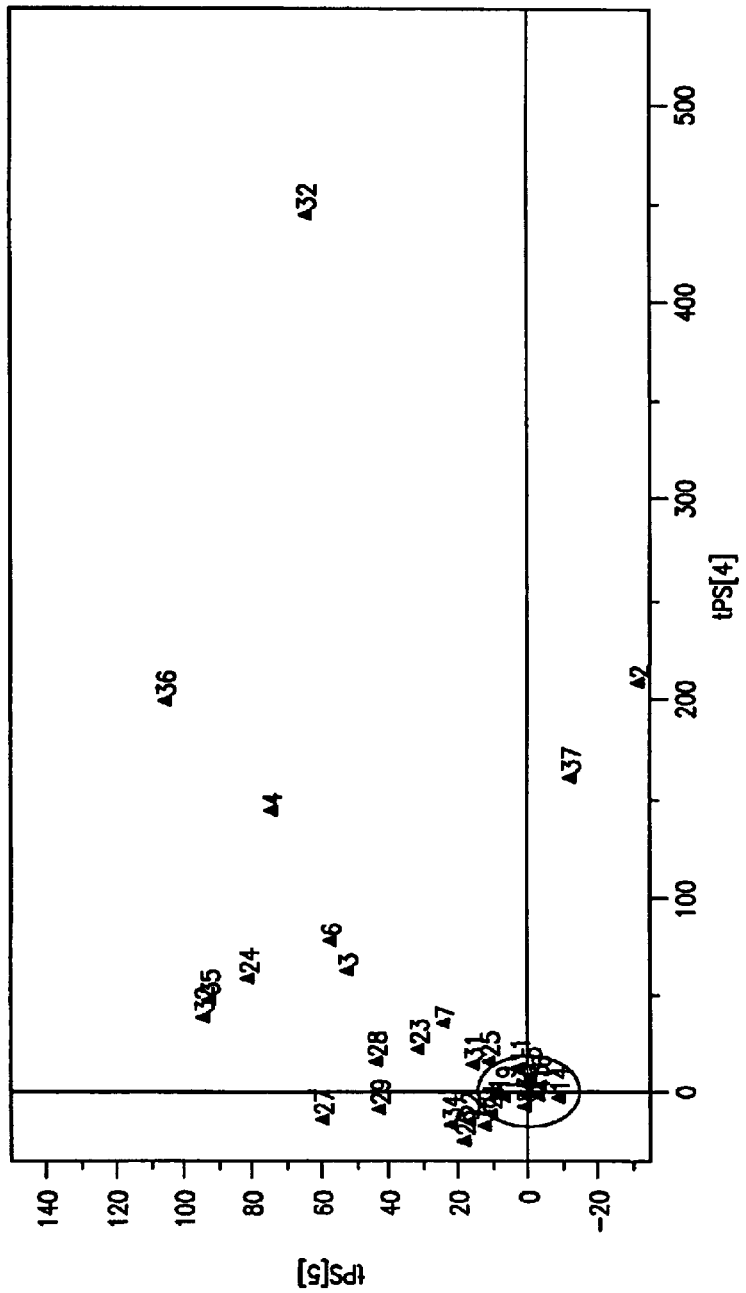
FIG. 20 is a scatter plot indicating the outlying compounds in example 4.
Figure 21:
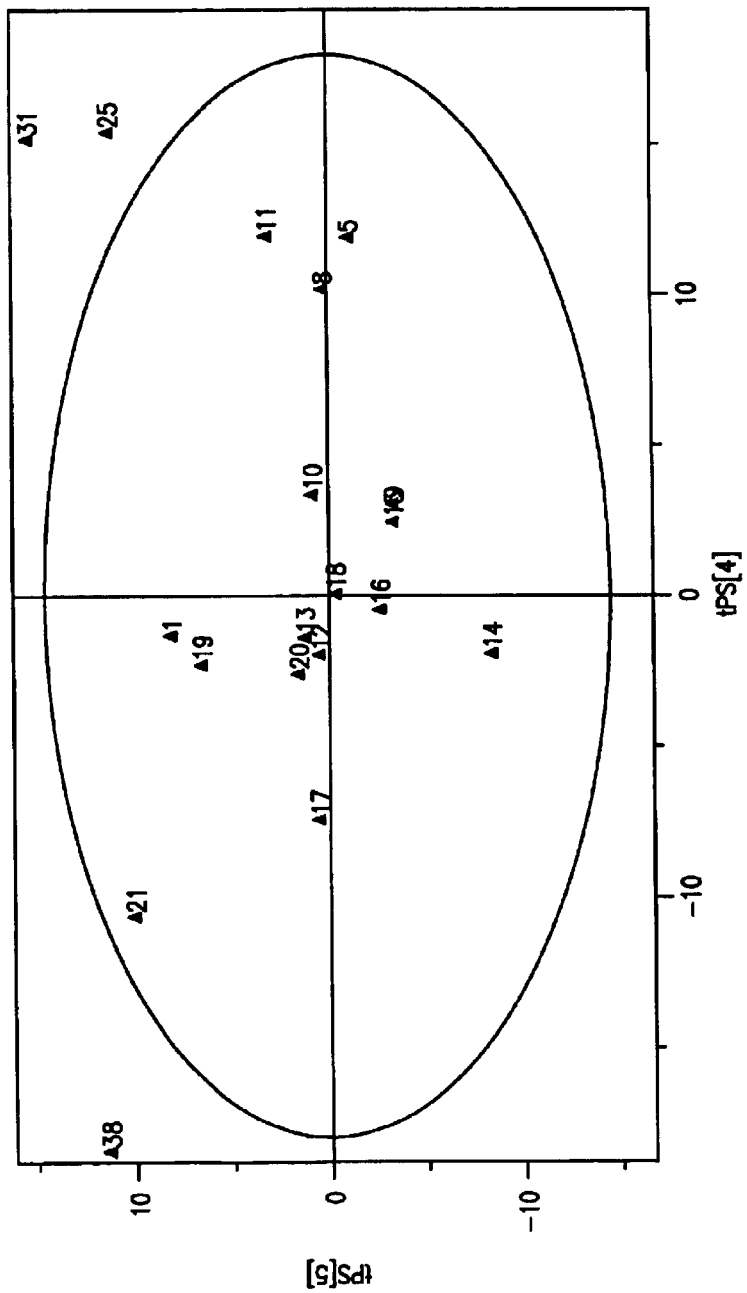
FIG. 21 is a scatter plot indicating compounds belonging to the family of structures in example 4.

The results of the PCA are depicted in the plots designated FIGS. 20 and 21. All Class IA data are present within the ellipse as can be seen most clearly in FIG. 21, whereas the Class IB are not, as shown in FIG. 20, with the exception of number 5 which has a fused ring structure analogous to the substructure present in the Class IA compounds.

III. Pharmacophore Analysis

The method of the present invention may also be employed to examine a pharmacophore by abstracting a model from a group of ligands. The physical structure in an idealized drug molecule which binds to the target region on a protein or other receptor target is known as a pharmacophore. Pharmacophore generation is a procedure to extract the most important common structural features relevant to a given biological activity from a series of molecules with a similar mechanism of action.

Figure 3:
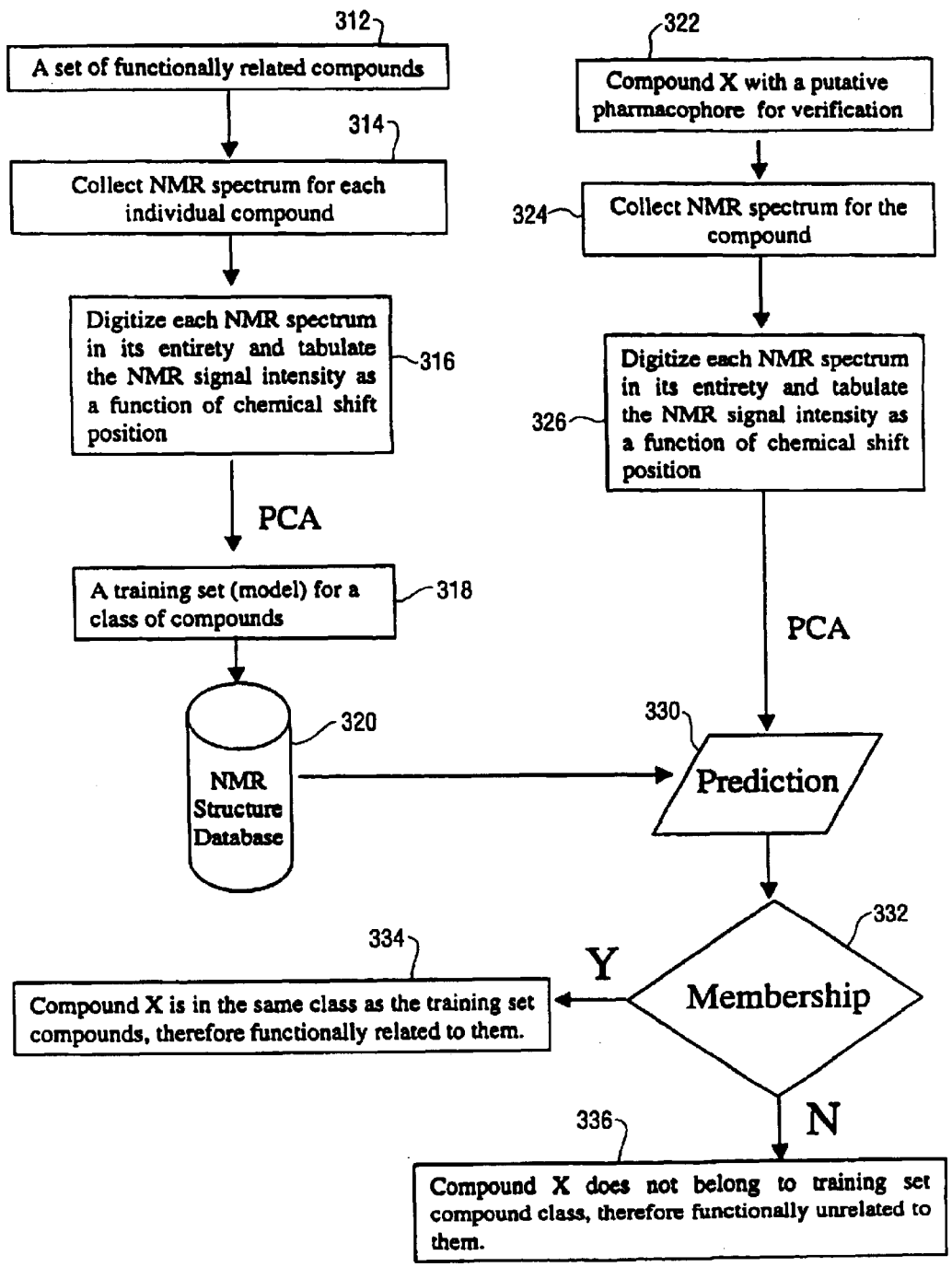
FIG. 3 is a flowchart illustrating a third embodiment of the present invention.

FIG. 3 is a flowchart depicting the third embodiment of the present invention. Initially, a set of functionally related compounds is selected (312). The functionally related compounds are typically related, preferably by binding to the same binding sites with similar efficiency, or they have some other biological activity in common.

NMR spectral data is collected for each of the selected compounds (314). Again, NMR chemical shift data for all NMR-active nuclei are used. As in the case of the first and second embodiments of the present invention, the use of 1-dimensional high field hydrogen-1 NMR spectroscopy is preferred however other one-dimensional NMR spectroscopy using other NMR-active nuclei, such as carbon-13 or nitrogen-15, may be used. Two- and three-dimensional NMR spectroscopy may also be used.

Each NMR spectrum is digitized, and the signal intensity is tabulated as a function of chemical shift position (316). Either the entire spectrum or a subset of the spectrum corresponding to areas of interest are used to produce the NMR signals analyzed. From these tabulated values, a first set of principal components of the signal intensities of the chemical shifts for nuclei found in each of the functionally related compounds is calculated forming a training set or model (318) for the family of compounds of interest. As before, the first set of principal components corresponds to the active nuclei in the training set. An NMR structure database (320) may be established to contain a plurality of models. Each model is directed to a separate pharmacophore.

An unknown compound (322) is selected for testing. The unknown compound may or may not belong to the functionally related set of compounds in question. The term "unknown" is used to refer to any compound tested, and need not be an actual unknown.

An NMR spectrum of the unknown compound is collected (324). The NMR spectrum may be one-, two- or three-dimensional NMR of any NMR-active nuclei found. The NMR data is of the same type for both the model and for the unknown and is preferably generated using the same reference compound. For high throughput NMR spectroscopy, for example when screening a library for drug leads, it is most preferred that the spectrum be a one-dimensional $^1$H NMR spectrum. Each NMR spectrum is digitized in its entirety and the NMR signal intensity is tabulated as a function of chemical shift position and is referred to herein as NMR signals (326).

PCA is performed on this digitized data and a second set of principal components is calculated composed of principal components in tabulated form. The second set of principal components is compared to the first set of principal components for "Prediction" (320) to determine PCA-based membership (332). Membership ascertains whether any member of the second set of principal components is clustered with the first set of principal components as determined by a statistical comparison means.

If the substructure is present, then the PCA score will be clustered with the training set (334). If the PCA score is not clustered with the training set then the unknown compound does not match the pharmacophore (336). The clustering is performed by a statistical comparison means such as T2 Hotelling Ellipse, Mahalanobis Distance, Heirarchical Clustering, and Mutually Exclusive analyses. The model validation considerations of this third embodiment are similar to those in the first and second embodiments.

An apparatus for creating a spectral model of a pharmacophore, including a spectrometer means for collecting NMR spectral measurements, a computer or computational means for handling and analyzing the data, and an output means for displaying the results, is also contemplated by the present invention.

IV. Quantification of Structural Diversity and Similarity

Furthermore, the present invention may be used to characterize structural diversity within a set of compounds. This embodiment is a modification of the previous embodiments with added analysis features. The magnitude of the values on the t1 and t2 axes, the ratio of such two magnitudes, or the area defined by the data points in the plot, either individually or collectively, can be used as a measure of compound diversity in the training set. The more structurally diverse the compounds in the training set, the greater the magnitude of the numbers on the t1 and t2 axes scales. The resultant information can be used to quantify and compare structural diversity and similarity of the resulting compounds.

It is to be understood that the present invention is not limited in scope to the specific embodiments described above, but encompasses any and all embodiments within the scope of the appended claims.

APPENDIX

Principal Component Analysis (PCA) is a least-squares technique that is also referred to as principal factor analysis. Factor analysis is a multivariate technique for reducing matrices of data to their lowest dimensionality by use of orthogonal factor space. The number of significant factors, referred to as principal components (PC), must be identified and used to model the data.

In the matrix form, PCA can be expressed as $$X=TP^c+E;$$

where X describes the original data, T is the score matrix, P' is a loading matrix or PCA factors, and E describes the residual error (typically noise). The score values represent the projections of the original samples in a given principal coordinate system defined by the loading vectors calculated from the original variables.

The spectral data matrix X contains the spectra of the n samples (or spectra) as columns of length m, where m is the number of data points (frequencies or wavelengths) per spectrum. The desired decomposition of these data can be accomplished by determining the eigenvectors and eigenvalues of the covariance matrix of X (the product of X by its transpose, $X^T$). $X^TX$ is thereby diagonalized. The resultant PCs are eigenvectors expressed in normalized spectral form.

The score matrix T summarizes the X-variables and determines the amplitude of each PC. The loading matrix P' shows the influence of the variables, and corresponds to the PCs. The score matrix is calculated:

$$T=X(PC)^T;$$

where PC is P'.

Thus X can be expressed as T(PC), such that $$T(PC)=X(PC)^T(PC)=X.$$

The PCs are orthogonal vectors oriented along the directions of maximal variance in X because they are the eigenvectors of $X^TX$. The residual error E is a matrix of the same dimensions as X.

The score matrix T is an n by f spectrum where f corresponds to the number of principal components, and P' is an f by m spectrum. See T. R. Brown and R. Stoyanova, "NMR Spectral Quantitation by Principal-Component Analysis. II. Determination of Frequency and Phase Shifts,"

*Journal of Magnetic Resonance. Series B*, 1996, 112, 32–43; see also R. Stoyanova, A. C. Kuesel, and T. R. Brown, "Communications Application of Principal-Component Analysis for NMR Spectral Quantitation," *Journal of Magnetic Resonance. Series A*, 1995, 115, 265–269.

Hotelling T2 is a statistical method for identifying outliers. The Hotelling T2 for observation i, based on A components is:

$$T_i^2 = \sum_{q=1}^{A} \frac{t_{ia}^2}{s_{ia}^2};$$

where $s_{ia}^2$ is the variance of $t_a$ according to the class model $T_i^2 \times N(N-A)/A(N^2-1)$ is F distributed with A and N–A degrees of freedom, N is the number of observations in the model training set and A is the number of components in the model or the selected number of components. Hence if $$T_i^2 > A(N^2-1)/N(N-A) \times F_{critical}(p=0.05),$$

then observation i is outside the 95% confidence region of the model. If p=0.1, then i is outside the 90% confidence region of the model. The confidence region for a two dimensional score plot of dimension a and b is an ellipse with axis $$s_{iaorb}^2 \times F2, N-2, a \times 2(N^2-1)/(N(N-2))^{1/2}.$$

What is claimed is:

1. A method for determining the presence of a specific molecular substructure in an organic compound, the method comprising:
   a) assembling a first set of selected nuclear magnetic resonance (NMR) spectral data from a group of organic compounds containing the specified substructure;
   b) assembling a second set of selected NMR spectral data from the organic compound being analyzed; and
   c) determining the presence or absence of the substructure in the organic compound by using a statistical comparison means to determine the relationship between the two data sets.

2. A method for determining the presence of a specific molecular substructure in an organic compound the method comprising:
   a) assembling a first set of selected NMR spectral data from a group of organic compounds containing the specified substructure;
   b) constructing a data training set model by subjecting the first set of data to principal component analysis;
   c) assembling a second set of NMR spectral data by calculating possible permutations of the NMR spectral data obtained for the organic compound;
   d) constructing a test set of values by subjecting the second set of data to principal component analysis; and
   e) confirming the presence or absence of the substructure in the organic compound by using a statistical comparison means to determine the relationship between the training set and the test set.

3. The method of claim 2 wherein the NMR spectral data consists of chemical shifts.

4. The method of claim 2 wherein the group of organic compounds is structurally related.

5. The method of claim 2 wherein the group of organic compounds is structurally diverse.

6. The method of claim 2 wherein the possible permutations are put in groups in accordance with the number of protons in the substructure.

7. The method of claim 2 wherein the statistical comparison means is selected from the group consisting of Principal Component or Factor Analysis, Mahalanobis Distance, Cluster Analysis (such as Hierarchical Clustering, and Mutually Exclusive Model).

8. The method of claim 2 wherein the NMR spectral data consists of NMR signal intensities.

9. A method for determining membership of organic compound in a family of compounds, the method comprising:
   a) providing a model of a training set of structurally related compounds each compound having membership in the family of compounds wherein the model is composed of a first set of principal components and each compound has active nuclei therein;
   b) calculating a second set of principal components from the intensities of the nuclear magnetic resonance signals corresponding to the organic compound;
   c) comparing the first and second sets of principal components; and
   d) determining whether any member of the second set of principal components is clustered with the first set of principal components by a statistical comparison means.

10. A method for constructing a spectral model of a pharmacophore, the method comprising:
    a) selecting a group of functionally related organic compounds with each compound having in common a specified biological activity, the causative pharmacopore and NMR-detectable nuclei;
    b) tabulating the NMR signals for the entire spectrum for each of the selected compounds; and
    c) generating a spectral model of the pharmacophore by subjecting the tabulated NMR signals to principal component analysis.

11. The method of claim 10 wherein the set of principle components constituting the model are calculated from corresponding selected regions of the full tabulated spectra.

12. The method of claim 10 further comprising a determination of the presence of the pharmacophore in an organic compound by:
    a) generating a test set of principal components from the NMR signals tabulated for the organic compound; and
    b) determining the presence or absence of the pharmacophore in the organic compound by using a statistical comparison means to determine the relationship between the two sets of principal components.

13. An apparatus for identifying a substructure of an organic compound, the apparatus comprising:
    a) spectrometer means for collecting a nuclear magnetic resonance spectral measurement of the organic compound wherein the nuclear magnetic resonance spectrum includes chemical shifts;
    b) computer means (i) for providing a model of a training set of compounds each compound having the substructure wherein the model is composed of a first set of principal components; (ii) for recording all the collected chemical shifts in the spectrum of the organic compound; (iii) for calculating possible permutations for the chemical shifts corresponding to the organic compound in distributions having the same number of chemical shifts as found in the substructure; (iv) for calculating a second set of principal components for each permutation (v) for comparing the first and second sets of principal components; and (vi) for determining whether any member of the second set of principal components is clustered with the first set of principal components; and c) output means for displaying whether any member of the second set of principal components is clustered with the first set of principal components by a statistical comparison means.

14. The apparatus of claim 13, wherein:

a) the spectrometer means further comprises collecting nuclear magnetic resonance spectrum of each individual compound in the set of structurally related compounds wherein the nuclear magnetic resonance spectrum includes chemical shifts; and b) the computer means further comprises (vi) for assigning selected nuclear magnetic resonance signals from the chemical shift data from each compound in the training set corresponding to the substructure of interest; (vii) for tabulating the chemical shift values as a function of the position of the substructure in each compound; (viii) for calculating the first set of principal components from the tabulated chemical shift values; and (ix) for generating a model of the training set of compounds each compound having the substructure.

15. An apparatus for determining membership of an organic compound in a family of compounds, the apparatus comprising:

a) spectrometer means for collecting a nuclear magnetic resonance spectrum of the organic compound wherein the nuclear magnetic resonance spectrum includes the nuclear magnetic resonance signals for the full spectral region detected;

b) computer means (i) for providing a model of a training set of structurally related compounds each compound having membership in the family of compounds wherein the model is composed of a first set of principal components and each compound has active nuclei therein; (ii) for recording all the collected nuclear magnetic resonance signals detected in the spectrum of the unknown compound; (iii) for calculating a second set of principal components from the intensities of the nuclear magnetic resonance signals detected for the entire spectrum corresponding to the unknown compound; (iv) for comparing the first and second sets of principal components; and (v) for determining whether any member of the second set of principal components is clustered with the first set of principal components by a statistical comparison means; and c) output means for displaying whether any member of the second set of principal components is clustered with the first set of principal components.

16. The apparatus of claim 15, wherein:

a) the spectrometer means further comprises collecting a nuclear magnetic resonance spectrum from each compound in the training set wherein the nuclear magnetic resonance spectrum includes the nuclear magnetic resonance signals for the full spectral region detected; and b) the computer means further comprises (vi) for assigning the nuclear magnetic resonance signals from the intensities of the nuclear magnetic resonance signals for the full spectral region detected corresponding to each compound in the training set; (vii) for tabulating the nuclear magnetic resonance signal values from the training set; (viii) for calculating the first set of principal components from the tabulated nuclear magnetic resonance signal values; and (ix) for generating a first set of principal components of the nuclear magnetic resonance signals found in each of the structurally related compounds wherein the first set of principal components taken together constitutes a model of the family of compounds.

17. An apparatus for determining the presence of a specific pharmacophore in an organic compound, the apparatus comprising:

a) spectrometer means for collecting a nuclear magnetic resonance spectrum of the organic compound wherein the nuclear magnetic resonance spectrum includes the nuclear magnetic resonance signals for the full spectral region detected;

b) computer means (i) for providing a model of a training set of functionally related compounds each compound having in common a biological activity; a causative pharmacophore, and NMR active nuclei wherein the model is composed of a first set of principal components and each compound having active nuclei therein; (ii) for recording all the collected nuclear magnetic resonance signals detected in the spectrum of the unknown compound; (iii) for calculating a second set of principal components from the intensities of the nuclear magnetic resonance signals detected for the entire spectrum corresponding to the unknown compound; (iv) for comparing the first and second sets of principal components; and (v) for determining whether any member of the second set of principal components is clustered with the first set of principal components by a statistical comparison means; and a) output means for displaying whether any member of the second set of principal components is clustered with the first let of principal components.

18. The apparatus of claim 17, wherein:

a) the spectrometer means further comprises collecting a nuclear magnetic resonance spectrum from each compound in the training set wherein the nuclear magnetic resonance spectrum includes the nuclear magnetic resonance signals for the full spectral region detected; and b) the computer means further comprises (vi) for assigning the nuclear magnetic resonance signals from the intensities of the nuclear magnetic resonance signals for the full spectral region detected corresponding to each compound in the training set; (vii) for tabulating the nuclear magnetic resonance signal values from the training set; (viii) for calculating the first set of principal components from the tabulated nuclear magnetic resonance signal values; and (ix) for generating a first set of principal components of the nuclear magnetic resonance signals found in each of the structurally related compounds wherein the first set of principal components taken together constitutes a model of the family of compounds.

* * * * *